(12) United States Patent
Nelson

(10) Patent No.: US 11,364,372 B2
(45) Date of Patent: *Jun. 21, 2022

(54) CHECK VALVE

(71) Applicant: ICU MEDICAL, INC., San Clemente, CA (US)

(72) Inventor: David Nelson, Irvine, CA (US)

(73) Assignee: ICU MEDICAL, INC., San Clemente, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 16/449,124

(22) Filed: Jun. 21, 2019

(65) Prior Publication Data
US 2020/0046961 A1    Feb. 13, 2020

Related U.S. Application Data

(63) Continuation of application No. 15/179,760, filed on Jun. 10, 2016, now Pat. No. 10,369,349, which is a
(Continued)

(51) Int. Cl.
*A61M 39/24* (2006.01)
*A61M 5/14* (2006.01)
(Continued)

(52) U.S. Cl.
CPC .......... *A61M 39/24* (2013.01); *A61M 5/1408* (2013.01); *A61M 39/10* (2013.01);
(Continued)

(58) Field of Classification Search
CPC ...... A61M 39/24; A61M 39/22; A61M 39/26; A61M 2039/2406; A61M 2039/242;
(Continued)

(56) References Cited

U.S. PATENT DOCUMENTS 274,447 A    3/1883   Kennish
724,445 A    4/1903   Decker
(Continued)

FOREIGN PATENT DOCUMENTS

CA    1 105 959    7/1981
CA    2 149 725    11/1995
(Continued)

OTHER PUBLICATIONS

Photographs of LifeShield CLAVE® & TKO-4S product, consisting of a needleless valve essentially as illustrated in Lopez (U.S. Pat. No. 5,685,866) and a flow control valve essentially as illustrated in Dikeman (U.S. Pat. No. 7,601,141), sold in the U.S. at least as early as May 2008.
(Continued)

*Primary Examiner* — James D Ponton
(74) *Attorney, Agent, or Firm* — Knobbe, Martens, Olson & Bear, LLP

(57) ABSTRACT

A check valve for use in a fluid pathway. The check valve may have a diaphragm and a plurality of supports extending from the diaphragm. The check valve and supports have a line of symmetry, and deformation of the check valve as it moves from a closed position to an opened position can be generally along the line of symmetry.

20 Claims, 20 Drawing Sheets

Related U.S. Application Data continuation of application No. PCT/US2014/068455, filed on Dec. 3, 2014.

(60) Provisional application No. 61/914,892, filed on Dec. 11, 2013.

(51) Int. Cl.
 *A61M 39/26* (2006.01)
 *F16K 15/14* (2006.01)
 *A61M 39/10* (2006.01)

(52) U.S. Cl.
 CPC .......... *A61M 39/26* (2013.01); *F16K 15/144* (2013.01); *A61M 2039/2446* (2013.01); *A61M 2039/2453* (2013.01); *A61M 2039/267* (2013.01); *A61M 2207/00* (2013.01)

(58) Field of Classification Search
 CPC .. A61M 2039/2426; A61M 2039/2433; A61M 2039/2446; A61M 2039/2453; A61M 2039/246; A61M 2039/2466; F16K 15/00; F16K 15/141; F16K 15/144; F16K 15/148; F16K 7/20; F16K 15/14; F16K 15/142; F16K 15/145; F16K 15/147; F16K 7/17
 See application file for complete search history.

(56) References Cited

U.S. PATENT DOCUMENTS

| | | | |
|---|---|---|---|
| 1,578,517 A | 3/1926 | Hein | |
| 1,923,501 A | 8/1933 | Perry | |
| 2,210,098 A | 8/1940 | Ravenscroft | |
| 2,289,677 A | 7/1942 | Perelson | |
| 2,347,988 A | 10/1943 | Burke | |
| 2,577,780 A | 12/1951 | Lockhart | |
| 2,688,979 A | 9/1954 | Kendrick | |
| 2,756,282 A | 7/1956 | Deane | |
| 2,756,740 A | 7/1956 | Deane | |
| 2,809,665 A | 10/1957 | Crowe | |
| 2,847,995 A | 8/1958 | Adams | |
| 2,999,499 A | 9/1961 | Willet | |
| 3,134,380 A | 5/1964 | Armao | |
| 3,135,261 A | 6/1964 | Carroll | |
| 3,171,412 A | 3/1965 | Braun | |
| 3,176,021 A | 3/1965 | Volungis et al. | |
| 3,191,655 A | 6/1965 | McCord | |
| 3,193,154 A | 7/1965 | Brass et al. | |
| 3,334,860 A | 8/1967 | Bolton, Jr. | |
| 3,352,531 A | 11/1967 | Kilmarx | |
| 3,354,881 A | 11/1967 | Bloch | |
| 3,385,301 A | 5/1968 | Harautuneian | |
| 3,502,097 A | 3/1970 | Muller | |
| 3,534,771 A | 10/1970 | Eyerdam et al. | |
| 3,570,484 A | 3/1971 | Steer et al. | |
| 3,630,199 A | 12/1971 | Gangarosa | |
| 3,648,684 A | 3/1972 | Barnwell et al. | |
| 3,659,602 A | 5/1972 | Cloyd | |
| 3,693,651 A * | 9/1972 | Gifford ................ | F16K 15/141 137/493 |
| 3,717,174 A | 2/1973 | Dewall | |
| 3,726,282 A | 4/1973 | Patel | |
| 26,939 A | 10/1973 | Ballard | |
| 3,788,519 A | 1/1974 | Mengel | |
| 3,830,241 A | 8/1974 | Dye et al. | |
| 3,831,629 A | 8/1974 | Mackal et al. | |
| 3,852,385 A | 12/1974 | Huggins | |
| 3,861,388 A | 1/1975 | Vaughn | |
| 3,889,675 A | 6/1975 | Stewart | |
| 3,896,853 A | 7/1975 | Bernhard | |
| D237,882 S | 12/1975 | Yamasaki | |
| 3,965,910 A | 6/1976 | Fisher | |
| 3,974,832 A | 8/1976 | Kruck | |
| 3,976,063 A | 8/1976 | Henneman et al. | |
| 3,976,073 A | 8/1976 | Quick et al. | |
| 3,977,403 A | 8/1976 | Patel | |
| 3,986,508 A | 10/1976 | Barrington | |
| 3,993,063 A | 11/1976 | Larrabee | |
| 3,994,293 A | 11/1976 | Ferro | |
| 4,005,710 A * | 2/1977 | Zeddies ................ | A61M 39/24 604/86 |
| 4,019,512 A | 4/1977 | Tenczar | |
| 4,022,205 A | 5/1977 | Tenczar | |
| 4,040,420 A | 8/1977 | Speer | |
| 4,076,285 A | 2/1978 | Martinez | |
| 4,079,738 A | 3/1978 | Dunn et al. | |
| 4,080,965 A | 3/1978 | Phillips | |
| 4,121,585 A | 10/1978 | Becker, Jr. | |
| 4,128,098 A | 12/1978 | Bloom et al. | |
| 4,133,441 A | 1/1979 | Mittleman et al. | |
| 4,143,853 A | 3/1979 | Abramson | |
| 4,149,535 A | 4/1979 | Volder | |
| 4,161,949 A | 7/1979 | Thanawalla | |
| 4,186,775 A | 2/1980 | Muroi | |
| 4,187,846 A | 2/1980 | Lolachi et al. | |
| 4,191,183 A | 3/1980 | Mendelson | |
| 4,198,983 A | 4/1980 | Becker et al. | |
| 4,200,096 A | 4/1980 | Charvin | |
| 4,214,779 A | 7/1980 | Losell | |
| 4,219,912 A | 9/1980 | Adams | |
| 4,243,034 A | 1/1981 | Brandt | |
| 4,244,378 A | 1/1981 | Brignola | |
| 4,257,416 A | 3/1981 | Prager | |
| D259,278 S | 5/1981 | McCaw et al. | |
| 4,294,249 A | 10/1981 | Sheehan et al. | |
| 4,294,250 A | 10/1981 | Dennehey | |
| 4,296,949 A | 10/1981 | Muetterties et al. | |
| 4,306,705 A | 12/1981 | Svensson | |
| D263,871 S | 4/1982 | Matsuura | |
| 4,324,239 A | 4/1982 | Gordon et al. | |
| 4,328,802 A | 5/1982 | Curley et al. | |
| 4,329,987 A | 5/1982 | Rogers et al. | |
| 4,334,551 A | 6/1982 | Pfister | |
| 4,338,933 A | 7/1982 | Bayard et al. | |
| 4,342,315 A | 8/1982 | Jackson | |
| 4,346,703 A | 8/1982 | Dennehey et al. | |
| 4,362,156 A | 12/1982 | Feller et al. | |
| 4,387,879 A | 6/1983 | Tauschinski | |
| RE31,315 E | 7/1983 | Jenkins et al. | |
| 4,392,851 A | 7/1983 | Elias | |
| 4,405,163 A | 9/1983 | Voges et al. | |
| 4,405,312 A | 9/1983 | Gross et al. | |
| 4,411,662 A | 10/1983 | Pearson | |
| 4,417,890 A | 11/1983 | Dennehey et al. | |
| 4,421,296 A | 12/1983 | Stephens | |
| 4,429,856 A | 2/1984 | Jackson | |
| 4,432,759 A | 2/1984 | Gross et al. | |
| 4,432,765 A | 2/1984 | Oscarsson | |
| 4,434,810 A | 3/1984 | Atkinson | |
| 4,439,188 A | 3/1984 | Dennehey et al. | |
| 4,439,193 A | 3/1984 | Larkin | |
| 4,449,693 A | 5/1984 | Gerea | |
| 4,457,749 A | 7/1984 | Bellotti et al. | |
| 4,483,368 A | 11/1984 | Panthafer | |
| 4,508,367 A | 4/1985 | Oreopoulos et al. | |
| 4,511,359 A | 4/1985 | Vaillancourt | |
| 4,512,766 A | 4/1985 | Vaillancourt | |
| 4,535,818 A | 8/1985 | Duncan et al. | |
| 4,535,820 A | 8/1985 | Raines | |
| 4,556,086 A | 12/1985 | Raines | |
| 4,564,054 A | 1/1986 | Gustavsson | |
| 4,566,480 A | 6/1986 | Parham | |
| 4,592,356 A | 6/1986 | Guiterrez | |
| 4,607,868 A | 8/1986 | Harvey et al. | |
| 4,610,469 A | 9/1986 | Wolff-Mooij | |
| 4,617,012 A | 10/1986 | Vaillancourt | |
| 4,619,640 A | 10/1986 | Poholshy et al. | |
| 4,621,654 A | 11/1986 | Holter | |
| 4,623,068 A | 11/1986 | Brown et al. | |
| 4,645,494 A | 2/1987 | Lee et al. | |
| 4,666,429 A | 5/1987 | Stone | |
| D290,656 S | 6/1987 | Kaleskas | |

(56) References Cited

U.S. PATENT DOCUMENTS

| | | |
|---|---|---|
| 4,673,400 A | 6/1987 | Martin |
| 4,676,228 A | 6/1987 | Krasner et al. |
| 4,683,916 A | 8/1987 | Raines |
| 4,706,487 A | 11/1987 | Bandou et al. |
| 4,710,168 A | 12/1987 | Schwab et al. |
| 4,725,267 A | 2/1988 | Vaillancourt |
| 4,730,635 A | 3/1988 | Linden |
| 4,752,292 A | 6/1988 | Lopez et al. |
| D296,592 S | 7/1988 | Wellenstam |
| 4,758,224 A | 7/1988 | Siposs |
| 4,759,756 A | 7/1988 | Forman et al. |
| 4,775,369 A | 10/1988 | Schwartz |
| 4,778,447 A | 10/1988 | Velde et al. |
| 4,778,453 A | 10/1988 | Lopez |
| 4,781,702 A | 11/1988 | Herrli |
| 4,804,015 A | 2/1989 | Albinsson |
| D300,177 S | 3/1989 | Bellotti et al. |
| D300,361 S | 3/1989 | Tokarz |
| 4,810,241 A | 3/1989 | Rogers et al. |
| 4,813,938 A | 3/1989 | Raulerson |
| 4,819,684 A | 4/1989 | Zaugg et al. |
| 4,832,214 A | 5/1989 | Schrader et al. |
| 4,834,664 A | 5/1989 | Lin |
| 4,834,716 A | 5/1989 | Ogle, II |
| D303,013 S | 8/1989 | Konopka |
| 4,871,353 A | 10/1989 | Thomsen |
| 4,874,377 A | 10/1989 | Newgard et al. |
| 4,878,897 A | 11/1989 | Katzin |
| 4,880,414 A | 11/1989 | Whipple |
| 4,883,456 A | 11/1989 | Holter |
| 4,889,527 A | 12/1989 | Herrli |
| 4,908,018 A | 3/1990 | Thomsen |
| 4,915,687 A | 4/1990 | Sivert |
| 4,917,668 A | 4/1990 | Haindl |
| 4,919,167 A | 4/1990 | Manska |
| 4,928,212 A | 5/1990 | Benavides |
| 4,934,657 A | 6/1990 | Dodson |
| 4,943,896 A | 7/1990 | Johnson |
| 4,946,445 A | 8/1990 | Lynn |
| 4,946,448 A | 8/1990 | Richmond |
| 4,963,133 A | 10/1990 | Whipple |
| 4,964,855 A | 10/1990 | Todd et al. |
| 4,966,199 A | 10/1990 | Ruschke |
| 4,969,883 A | 11/1990 | Gilbert et al. |
| D314,050 S | 1/1991 | Sone |
| 4,985,399 A | 1/1991 | Matsuda et al. |
| 4,987,181 A | 1/1991 | Bichon et al. |
| 4,991,413 A | 2/1991 | Arnalda |
| 4,991,629 A | 2/1991 | Ernesto et al. |
| 4,991,745 A | 2/1991 | Brown |
| 4,995,863 A | 2/1991 | Nichols et al. |
| 4,998,713 A | 3/1991 | Vaillancourt |
| 4,998,927 A | 3/1991 | Vaillancourt |
| 5,006,114 A | 4/1991 | Rogers et al. |
| 5,009,490 A | 4/1991 | Kuono et al. |
| 5,018,532 A | 5/1991 | Ethridge, III |
| 5,024,657 A | 6/1991 | Needham et al. |
| 5,030,210 A | 7/1991 | Alchas |
| 5,031,675 A | 7/1991 | Lindqren |
| 5,041,087 A | 8/1991 | Loo et al. |
| 5,046,456 A | 9/1991 | Heyman et al. |
| 5,049,128 A | 9/1991 | Duquette |
| D321,250 S | 10/1991 | Jepson et al. |
| D321,251 S | 10/1991 | Jepson et al. |
| 5,061,253 A | 10/1991 | Yoshida |
| 5,064,416 A | 11/1991 | Newgard |
| 5,065,783 A | 11/1991 | Ogle, II |
| 5,071,411 A | 12/1991 | Hillstead |
| 5,098,385 A | 3/1992 | Walsh |
| 5,098,405 A | 3/1992 | Peterson et al. |
| 5,098,406 A | 3/1992 | Sawyer |
| 5,100,394 A | 3/1992 | Dudar et al. |
| 5,108,380 A | 4/1992 | Heritze et al. |
| 5,114,408 A | 5/1992 | Fleischhaker et al. |
| 5,116,361 A | 5/1992 | Kim et al. |
| 5,122,123 A | 6/1992 | Vaillancourt |
| 5,125,915 A | 6/1992 | Berry et al. |
| 5,135,489 A | 8/1992 | Jepson et al. |
| 5,137,524 A | 8/1992 | Lynn et al. |
| 5,147,333 A | 9/1992 | Raines |
| 5,154,703 A | 10/1992 | Bonaldo |
| 5,156,600 A | 10/1992 | Young |
| 5,158,554 A | 10/1992 | Jepson et al. |
| 5,163,922 A | 11/1992 | McElveen, Jr. et al. |
| 5,167,238 A | 12/1992 | Newman |
| 5,167,636 A | 12/1992 | Clement |
| 5,171,234 A | 12/1992 | Jepson et al. |
| 5,180,761 A | 1/1993 | Shiao |
| 5,188,620 A | 2/1993 | Jepson et al. |
| 5,190,067 A | 3/1993 | Paradis et al. |
| 5,199,947 A | 4/1993 | Lopez et al. |
| 5,201,717 A | 4/1993 | Wyatt et al. |
| 5,201,722 A | 4/1993 | Moorehead et al. |
| 5,203,775 A | 4/1993 | Frank et al. |
| 5,211,638 A | 5/1993 | Dudar et al. |
| 5,215,538 A | 6/1993 | Larkin |
| 5,221,271 A | 6/1993 | Nicholson et al. |
| 5,224,515 A | 7/1993 | Foster et al. |
| 5,242,393 A | 9/1993 | Brimhall et al. |
| 5,242,423 A | 9/1993 | Goodsir et al. |
| 5,242,425 A | 9/1993 | White et al. |
| 5,242,432 A | 9/1993 | DeFrank |
| 5,249,598 A | 10/1993 | Schmidt |
| 5,251,873 A | 10/1993 | Atkinson et al. |
| 5,253,842 A | 10/1993 | Huebscher et al. |
| 5,255,676 A | 10/1993 | Russo |
| 5,256,155 A | 10/1993 | Yerlikaya et al. |
| 5,267,966 A | 12/1993 | Paul |
| 5,269,771 A | 12/1993 | Thomas et al. |
| 5,273,533 A | 12/1993 | Bonaldo |
| 5,280,876 A | 1/1994 | Atkins |
| D344,585 S | 2/1994 | Morse |
| 5,284,475 A | 2/1994 | Mackal |
| 5,290,254 A | 3/1994 | Vaillancourt |
| 5,292,308 A | 3/1994 | Ryan |
| 5,293,902 A | 3/1994 | Lapierie |
| 5,295,657 A | 3/1994 | Atkinson |
| 5,295,658 A | 3/1994 | Atkinson et al. |
| D346,011 S | 4/1994 | Hawkins |
| 5,301,686 A | 4/1994 | Newman |
| 5,306,265 A | 4/1994 | Ragazzi |
| 5,312,083 A | 5/1994 | Ekman |
| 5,312,377 A | 5/1994 | Dalhon |
| 5,322,518 A | 6/1994 | Schneider |
| 5,324,270 A | 6/1994 | Kayon et al. |
| 5,336,192 A | 8/1994 | Palestrant |
| 5,342,316 A | 8/1994 | Wallace |
| 5,342,326 A | 8/1994 | Peppel et al. |
| 5,344,414 A | 9/1994 | Lopez et al. |
| 5,348,542 A | 9/1994 | Ellis |
| 5,353,837 A | 10/1994 | Faust |
| 5,356,375 A | 10/1994 | Higley |
| 5,356,396 A | 10/1994 | Wyatt et al. |
| 5,360,413 A | 11/1994 | Leason et al. |
| 5,380,306 A | 1/1995 | Brinon |
| 5,389,086 A | 2/1995 | Attermeier et al. |
| 5,391,150 A | 2/1995 | Richmond |
| 5,398,530 A | 3/1995 | Derman |
| 5,401,245 A | 3/1995 | Haining |
| D357,736 S | 4/1995 | Dye |
| 5,402,826 A | 4/1995 | Molnar et al. |
| 5,402,982 A | 4/1995 | Atkinson et al. |
| 5,407,437 A | 4/1995 | Heimreid |
| 5,409,471 A | 4/1995 | Atkinson et al. |
| 5,395,348 A | 5/1995 | Ryan |
| 5,411,483 A | 5/1995 | Loomas et al. |
| 5,411,499 A | 5/1995 | Dudar et al. |
| 5,417,673 A | 5/1995 | Gordon |
| 5,439,451 A | 8/1995 | Collinson et al. |
| 5,439,452 A | 8/1995 | McCarty |
| 5,441,487 A | 8/1995 | Vedder |
| 5,442,941 A | 8/1995 | Kahonen et al. |
| 5,453,097 A | 9/1995 | Paradis |
| 5,456,676 A | 10/1995 | Nelson et al. |

(56) References Cited

U.S. PATENT DOCUMENTS

| | | |
|---|---|---|
| 5,462,255 A | 10/1995 | Rosen et al. |
| D363,988 S | 11/1995 | Dye |
| D364,459 S | 11/1995 | Dye |
| D364,460 S | 11/1995 | Dye |
| D364,680 S | 11/1995 | Dye |
| 5,465,938 A | 11/1995 | Werge et al. |
| 5,470,319 A | 11/1995 | Mayer |
| 5,474,544 A | 12/1995 | Lynn |
| 5,480,393 A | 1/1996 | Bommarito |
| 5,487,731 A | 1/1996 | Denton |
| D367,714 S | 3/1996 | Pennicook |
| 5,501,426 A | 3/1996 | Atkinson et al. |
| 5,501,526 A | 3/1996 | Asai et al. |
| D368,737 S | 4/1996 | Dunn et al. |
| 5,509,433 A | 4/1996 | Paradis |
| 5,514,116 A | 5/1996 | Vaillancourt et al. |
| 5,520,665 A | 5/1996 | Fleetwood |
| 5,522,804 A | 6/1996 | Lynn |
| 5,533,708 A | 7/1996 | Atkinson et al. |
| 5,533,996 A | 7/1996 | Murphey et al. |
| 5,535,771 A | 7/1996 | Purdy et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| D373,633 S | 9/1996 | La Motte |
| 5,554,136 A | 9/1996 | Luther |
| 5,555,908 A | 9/1996 | Edwards et al. |
| 5,556,388 A | 9/1996 | Johlin, Jr. |
| 5,562,632 A | 10/1996 | Davila et al. |
| 5,569,235 A | 10/1996 | Ross et al. |
| 5,573,516 A | 11/1996 | Tyner |
| 5,577,706 A | 11/1996 | King |
| 5,578,059 A | 11/1996 | Patzer |
| 5,597,536 A | 1/1997 | Mayer |
| 5,674,206 A | 1/1997 | Allton et al. |
| 5,603,706 A | 2/1997 | Wyatt et al. |
| 5,609,584 A | 3/1997 | Gettig et al. |
| 5,616,129 A | 4/1997 | Mayer |
| 5,616,130 A | 4/1997 | Mayer |
| 5,617,897 A | 4/1997 | Myers |
| 5,620,424 A | 4/1997 | Abramson |
| 5,620,434 A | 4/1997 | Brony |
| 5,624,414 A | 4/1997 | Boettger |
| 5,632,735 A | 5/1997 | Wyatt et al. |
| 5,639,810 A | 6/1997 | Smith, III et al. |
| 5,645,538 A | 7/1997 | Richmond |
| 5,660,205 A | 8/1997 | Epstein |
| 5,667,500 A | 9/1997 | Palmer et al. |
| 5,669,891 A | 9/1997 | Vaillancourt |
| 5,676,346 A | 10/1997 | Leinsing |
| 5,685,866 A | 11/1997 | Lopez |
| 5,690,612 A | 11/1997 | Lopez et al. |
| 5,690,865 A | 11/1997 | Kindt-Larsen et al. |
| 5,694,686 A | 12/1997 | Lopez |
| 5,695,466 A | 12/1997 | Lopez et al. |
| 5,699,821 A | 12/1997 | Paradis |
| 5,700,248 A | 12/1997 | Lopez |
| 5,728,751 A | 3/1998 | Patnaik |
| 5,730,418 A | 3/1998 | Feith et al. |
| 5,738,663 A | 4/1998 | Lopez |
| 5,749,861 A | 5/1998 | Guala et al. |
| D394,898 S | 6/1998 | Evans |
| 5,769,825 A | 6/1998 | Lynn |
| 5,775,671 A | 7/1998 | Cote, Sr. |
| 5,776,113 A | 7/1998 | Daugherty et al. |
| 5,782,816 A | 7/1998 | Werschmidt et al. |
| 5,785,693 A | 7/1998 | Haining |
| 5,788,215 A | 8/1998 | Ryan |
| 5,797,897 A | 8/1998 | Jepson et al. |
| 5,806,551 A | 9/1998 | Meloul et al. |
| 5,806,831 A | 9/1998 | Paradis |
| 5,807,348 A | 9/1998 | Zinger et al. |
| 5,810,789 A | 9/1998 | Powers et al. |
| D400,263 S | 10/1998 | Shugart |
| 5,817,068 A | 10/1998 | Urrutia |
| 5,817,069 A | 10/1998 | Arnett |
| 5,820,601 A | 10/1998 | Mayer |
| 5,833,213 A | 11/1998 | Ryan |
| 5,836,923 A | 11/1998 | Mayer |
| 5,839,715 A | 11/1998 | Leinsing |
| 5,843,044 A | 12/1998 | Moorehead |
| 5,843,046 A | 12/1998 | Motisi et al. |
| 5,846,233 A | 12/1998 | Lilley et al. |
| 5,865,807 A | 2/1999 | Blake, III |
| 5,873,862 A | 2/1999 | Lopez |
| 5,882,348 A | 3/1999 | Winterton et al. |
| 5,899,888 A | 5/1999 | Jepson et al. |
| 5,901,942 A | 5/1999 | Lopez |
| 5,911,710 A | 6/1999 | Barry et al. |
| 5,928,204 A | 7/1999 | Lopez |
| 5,935,620 A | 8/1999 | Baudin |
| 5,947,954 A | 9/1999 | Bonaldo |
| 5,954,313 A | 9/1999 | Ryan |
| 5,957,898 A | 9/1999 | Jepson et al. |
| 5,967,490 A | 10/1999 | Pike |
| 5,979,868 A | 11/1999 | Wu et al. |
| 5,984,903 A | 11/1999 | Nadal |
| D418,916 S | 1/2000 | Bastable |
| 6,009,902 A | 1/2000 | Troiani et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| 6,048,335 A | 4/2000 | Mayer |
| 6,050,978 A | 4/2000 | Orr et al. |
| 6,063,062 A | 5/2000 | Paradis |
| 6,079,432 A | 6/2000 | Paradis |
| 6,089,541 A | 7/2000 | Weinheier et al. |
| 6,099,511 A | 8/2000 | Devos et al. |
| 6,113,068 A | 9/2000 | Ryan |
| 6,116,571 A | 9/2000 | Hettinger |
| 6,117,114 A | 9/2000 | Paradis |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,162,206 A | 12/2000 | Bindokas et al. |
| 6,162,251 A | 12/2000 | Kredovski |
| 6,168,137 B1 | 1/2001 | Paradis |
| 6,170,800 B1 | 1/2001 | Meloul et al. |
| 6,171,287 B1 | 1/2001 | Lynn |
| 6,177,037 B1 | 1/2001 | Mayer |
| 6,183,448 B1 | 2/2001 | Mayer |
| 6,189,859 B1 | 2/2001 | Rohrbough et al. |
| D438,955 S | 3/2001 | Rudzena |
| 6,206,861 B1 | 3/2001 | Mayer |
| 6,210,624 B1 | 4/2001 | Mayer |
| 6,213,996 B1 | 4/2001 | Jepson et al. |
| 6,228,065 B1 | 5/2001 | Lynn |
| 6,228,069 B1 | 5/2001 | Barth et al. |
| 6,245,048 B1 | 6/2001 | Fangrow et al. |
| 6,254,579 B1 | 7/2001 | Cogger et al. |
| 6,261,282 B1 | 7/2001 | Jepson et al. |
| 6,261,630 B1 | 7/2001 | Nazarova et al. |
| 6,279,783 B1 | 8/2001 | Brown et al. |
| 6,290,206 B1 | 9/2001 | Doyle |
| 6,299,131 B1 | 10/2001 | Ryan |
| 6,299,132 B1 | 10/2001 | Wienheimer |
| 6,325,782 B1 | 12/2001 | Lopez |
| D454,637 S | 3/2002 | Netenborg |
| 6,364,861 B1 | 4/2002 | Feith et al. |
| 6,364,869 B1 | 4/2002 | Bonaldo |
| 6,390,130 B1 | 5/2002 | Guala |
| 6,428,520 B1 | 8/2002 | Lopez et al. |
| 6,444,324 B1 | 9/2002 | Yang et al. |
| 6,482,188 B1 | 11/2002 | Rogers et al. |
| D468,015 S | 12/2002 | Horppu |
| D468,016 S | 12/2002 | Mosler et al. |
| 6,530,504 B2 | 3/2003 | Socier |
| 6,541,802 B2 | 4/2003 | Doyle |
| 6,543,745 B1 | 4/2003 | Enerson |
| D475,795 S | 6/2003 | Johnson et al. |

(56) References Cited

U.S. PATENT DOCUMENTS

| | | |
|---|---|---|
| 6,572,592 B1 | 6/2003 | Lopez |
| 6,585,229 B2 | 7/2003 | Cote, Sr. et al. |
| 6,595,964 B2 | 7/2003 | Finley et al. |
| 6,595,981 B2 | 7/2003 | Huet |
| 6,599,273 B1 | 7/2003 | Lopez |
| 6,605,076 B1 | 8/2003 | Jepson et al. |
| 6,609,696 B2 | 8/2003 | Enerson |
| 6,635,044 B2 | 10/2003 | Lopez |
| 6,651,956 B2 | 11/2003 | Miller |
| 6,656,517 B2 | 12/2003 | Michal et al. |
| 6,669,673 B2 | 12/2003 | Lopez |
| 6,669,681 B2 | 12/2003 | Jepson et al. |
| 6,673,053 B2 | 1/2004 | Wang et al. |
| 6,682,509 B2 | 1/2004 | Lopez |
| 6,689,109 B2 | 2/2004 | Lynn |
| 6,695,817 B1 | 2/2004 | Fangrow, Jr. |
| 6,706,022 B1 | 3/2004 | Leinsing et al. |
| 6,712,791 B2 | 3/2004 | Lui et al. |
| 6,727,294 B2 | 4/2004 | Kanayama et al. |
| 6,740,063 B2 | 5/2004 | Lynn |
| 6,745,998 B2 | 6/2004 | Doyle |
| 6,755,391 B2 | 6/2004 | Newton et al. |
| 6,758,833 B2 | 7/2004 | Lopez |
| 6,783,709 B2 | 8/2004 | Harreld et al. |
| 6,802,490 B2 | 10/2004 | Leinsing |
| 6,808,161 B1 | 10/2004 | Hishikawa |
| 6,832,994 B2 | 12/2004 | Niedospial, Jr. et al. |
| 6,840,501 B2 | 1/2005 | Doyle |
| 6,848,139 B2 | 2/2005 | Simon et al. |
| 6,866,656 B2 | 3/2005 | Tingey et al. |
| 6,869,426 B2 | 3/2005 | Ganem |
| 6,871,838 B2 | 3/2005 | Raines et al. |
| 6,883,778 B1 | 4/2005 | Newton et al. |
| 6,892,998 B2 | 5/2005 | Newton |
| 6,908,459 B2 | 6/2005 | Harding et al. |
| 6,916,309 B2 | 7/2005 | Fangrow, Jr. |
| 6,932,795 B2 | 8/2005 | Lopez et al. |
| 6,964,406 B2 | 11/2005 | Doyle |
| 6,991,215 B2 | 1/2006 | Kiehne |
| 6,994,315 B2 | 2/2006 | Ryan et al. |
| 6,997,917 B2 | 2/2006 | Niedospial, Jr. et al. |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt |
| 7,044,441 B2 | 5/2006 | Doyle |
| 7,074,216 B2 | 7/2006 | Fowles et al. |
| 7,100,890 B2 | 9/2006 | Cote et al. |
| 7,104,520 B2 | 9/2006 | Leinsing et al. |
| 7,114,701 B2 | 10/2006 | Peppel |
| 7,125,396 B2 | 10/2006 | Leinsing et al. |
| 7,140,592 B2 | 11/2006 | Phillips et al. |
| 7,184,825 B2 | 2/2007 | Leinsing et al. |
| D546,946 S | 7/2007 | Blake |
| D547,862 S | 7/2007 | Dikeman et al. |
| 7,244,249 B2 | 7/2007 | Leinsing et al. |
| 7,252,652 B2 | 8/2007 | Moorehead et al. |
| 7,264,859 B2 | 9/2007 | Souns et al. |
| D557,281 S | 12/2007 | Miller et al. |
| D557,283 S | 12/2007 | Miller et al. |
| 7,306,197 B2 | 12/2007 | Parrino et al. |
| 7,306,199 B2 | 12/2007 | Leinsing et al. |
| 7,314,061 B2 | 1/2008 | Peppel |
| 7,326,188 B1 | 2/2008 | Russell et al. |
| 7,329,249 B2 | 2/2008 | Bonaldo |
| 7,335,182 B1 | 2/2008 | Hilaire |
| D567,941 S | 4/2008 | Dikeman et al. |
| 7,357,792 B2 | 4/2008 | Newton et al. |
| D568,466 S | 5/2008 | Dikeman et al. |
| D569,391 S | 5/2008 | Miller et al. |
| D569,506 S | 5/2008 | Dikeman et al. |
| D570,880 S | 6/2008 | Miller et al. |
| 7,396,348 B2 | 7/2008 | Newton et al. |
| 7,422,369 B2 | 9/2008 | Bergman et al. |
| 7,470,261 B2 | 12/2008 | Lynn |
| 7,470,262 B2 | 12/2008 | Hiejima et al. |
| 7,497,848 B2 | 3/2009 | Leinsing et al. |
| 7,497,849 B2 | 3/2009 | Fangrow, Jr. |
| 7,510,545 B2 | 3/2009 | Peppel |
| 7,520,489 B2 | 4/2009 | Rushke |
| 7,530,546 B2 | 5/2009 | Ryan et al. |
| 7,533,696 B2 | 5/2009 | Paul, Jr. |
| 7,556,060 B2 | 7/2009 | Guala |
| 7,559,530 B2 | 7/2009 | Korogi et al. |
| 7,563,243 B2 | 7/2009 | Mendels |
| 7,581,561 B2 | 9/2009 | Funamura et al. |
| 7,584,767 B2 | 9/2009 | Funamura et al. |
| 7,588,563 B2 | 9/2009 | Guala |
| 7,591,449 B2 | 9/2009 | Raines et al. |
| 7,600,530 B2 | 10/2009 | Truitt et al. |
| 7,601,141 B2 | 10/2009 | Dikeman et al. |
| 7,615,035 B2 | 11/2009 | Peppel |
| 7,624,749 B2 | 12/2009 | Guala |
| 7,625,359 B2 | 12/2009 | Guala |
| 7,628,774 B2 | 12/2009 | Fangrow, Jr. |
| 7,645,274 B2 | 1/2010 | Whitley |
| 7,651,481 B2 | 1/2010 | Raybuck |
| 7,666,170 B2 | 2/2010 | Guala |
| 7,673,653 B2 | 3/2010 | Mijers et al. |
| 7,691,090 B2 | 4/2010 | Belley et al. |
| 7,703,486 B2 | 4/2010 | Costanzo |
| 7,713,250 B2 | 5/2010 | Harding et al. |
| 7,717,882 B2 | 5/2010 | Harding |
| 7,717,886 B2 | 5/2010 | Lopez |
| 7,743,799 B2 | 6/2010 | Mosier et al. |
| 7,753,338 B2 | 7/2010 | Desecki |
| 7,753,892 B2 | 7/2010 | Newton et al. |
| 7,758,566 B2 | 7/2010 | Simpson et al. |
| 7,763,013 B2 | 7/2010 | Baldwin et al. |
| 7,763,199 B2 | 7/2010 | Fangrow |
| 7,771,383 B2 | 8/2010 | Truitt et al. |
| 7,784,766 B2 | 8/2010 | Guala |
| 7,806,873 B2 | 10/2010 | Dikeman et al. |
| 7,815,168 B2 | 10/2010 | Vangsness et al. |
| 7,824,393 B2 | 11/2010 | Fangrow, Jr. |
| 7,837,658 B2 | 11/2010 | Cote, Sr. et al. |
| 7,841,581 B2 | 11/2010 | Thorne, Jr. et al. |
| 7,842,026 B2 | 11/2010 | Cahill et al. |
| 7,857,284 B2 | 12/2010 | Kimball et al. |
| 7,857,285 B2 | 12/2010 | Lee et al. |
| 7,857,802 B2 | 12/2010 | Brandenburger et al. |
| 7,857,805 B2 | 12/2010 | Raines |
| 7,862,537 B2 | 1/2011 | Zinger et al. |
| 7,867,204 B2 | 1/2011 | Bartholomew et al. |
| 7,879,012 B2 | 2/2011 | Kane et al. |
| 7,879,013 B2 | 2/2011 | Smith et al. |
| 7,900,659 B2 | 3/2011 | Whitley et al. |
| 7,905,873 B2 | 3/2011 | Rondeau et al. |
| 7,909,056 B2 | 3/2011 | Truitt et al. |
| 7,914,502 B2 | 3/2011 | Newton et al. |
| D638,933 S | 5/2011 | Hill |
| 7,947,032 B2 | 5/2011 | Harding et al. |
| 7,954,515 B2 | 6/2011 | Gerst |
| 7,959,614 B2 | 6/2011 | Dikeman et al. |
| 7,967,797 B2 | 6/2011 | Winsor et al. |
| 7,975,722 B2 | 7/2011 | Kiehne |
| 7,981,090 B2 | 7/2011 | Plishka et al. |
| 7,981,381 B2 | 7/2011 | Lurvey et al. |
| 7,984,730 B2 | 7/2011 | Ziv et al. |
| 7,985,206 B2 | 7/2011 | Dikeman et al. |
| D643,920 S | 8/2011 | Gil Pascual |
| 7,988,128 B2 | 8/2011 | Wentling |
| 7,993,328 B2 | 8/2011 | Whitley |
| 7,998,122 B2 | 8/2011 | Lynn et al. |
| 7,998,134 B2 | 8/2011 | Fangrow |
| 8,006,953 B2 | 8/2011 | Bennett |
| D644,731 S | 9/2011 | Fang, Jr. |
| 8,015,990 B2 | 9/2011 | Pascal et al. |
| 8,021,354 B2 | 9/2011 | Huang |
| 8,034,021 B2 | 10/2011 | Mendels |
| 8,034,035 B2 | 10/2011 | Weaver et al. |
| 8,038,663 B2 | 10/2011 | Miner |
| 8,042,838 B2 | 10/2011 | Buckler et al. |
| 8,048,038 B2 | 11/2011 | Guala |

(56) References Cited

U.S. PATENT DOCUMENTS

| | | |
|---|---|---|
| 8,052,648 B2 | 11/2011 | Dikeman et al. |
| 8,057,442 B2 | 11/2011 | Dikeman et al. |
| 8,062,266 B2 | 11/2011 | McKinnon et al. |
| 8,062,267 B2 | 11/2011 | McKinnon et al. |
| 8,062,280 B2 | 11/2011 | Jepson et al. |
| 8,066,648 B1 | 11/2011 | Mark |
| 8,066,669 B2 | 11/2011 | Christensen et al. |
| 8,066,670 B2 | 11/2011 | Cluff et al. |
| 8,070,189 B2 | 12/2011 | Yow et al. |
| 8,070,725 B2 | 12/2011 | Christensen |
| 8,074,964 B2 | 12/2011 | Mansour et al. |
| 8,092,432 B2 | 1/2012 | Nordgren |
| 8,096,525 B2 | 1/2012 | Ryan |
| 8,100,868 B2 | 1/2012 | Newton et al. |
| 8,100,869 B2 | 1/2012 | Vangsness et al. |
| 8,105,314 B2 | 1/2012 | Fangrow |
| D654,166 S | 2/2012 | Lair |
| D655,000 S | 2/2012 | Mirigian |
| 8,122,923 B2 | 2/2012 | Kraus et al. |
| 8,123,738 B2 | 2/2012 | Vaillancourt |
| 8,133,209 B2 | 3/2012 | Guala |
| 8,136,330 B2 | 3/2012 | Ostler et al. |
| 8,137,303 B2 | 3/2012 | Stout et al. |
| 8,142,403 B2 | 3/2012 | Carlyon |
| 8,152,790 B2 | 4/2012 | Lopez et al. |
| 8,156,971 B2 | 4/2012 | Costanzo |
| 8,157,784 B2 | 4/2012 | Rogers |
| 8,162,006 B2 | 4/2012 | Guala |
| 8,162,013 B2 | 4/2012 | Rosenquist et al. |
| 8,162,914 B2 | 4/2012 | Kraushaar et al. |
| 8,167,863 B2 | 5/2012 | Yow |
| 8,172,823 B2 | 5/2012 | Rondeau et al. |
| 8,177,760 B2 | 5/2012 | Rome et al. |
| 8,177,768 B2 | 5/2012 | Leinsing |
| 8,177,772 B2 | 5/2012 | Christensen et al. |
| 8,182,452 B2 | 5/2012 | Mansour et al. |
| 8,197,452 B2 | 6/2012 | Harding et al. |
| 8,197,466 B2 | 6/2012 | Yokota et al. |
| 8,211,089 B2 | 7/2012 | Winsor et al. |
| 8,221,363 B2 | 7/2012 | Jepson |
| 8,221,391 B2 | 7/2012 | Fangrow, Jr. |
| 8,235,971 B2 | 8/2012 | Christensen et al. |
| 8,241,268 B2 | 8/2012 | Whitley |
| 8,277,424 B2 | 10/2012 | Pan |
| 8,286,657 B2 | 10/2012 | Belley et al. |
| 8,286,936 B2 | 10/2012 | Kitani et al. |
| 8,287,518 B2 | 10/2012 | Kitani et al. |
| 8,298,195 B2 | 10/2012 | Peppel |
| 8,298,196 B1 | 10/2012 | Mansour |
| 8,328,769 B2 | 12/2012 | Dikeman et al. |
| 8,337,483 B2 | 12/2012 | Harding et al. |
| 8,361,408 B2 | 1/2013 | Lynn |
| 8,366,658 B2 | 2/2013 | Davis et al. |
| 8,366,676 B2 | 2/2013 | Harding et al. |
| 8,372,043 B2 | 2/2013 | Grimm et al. |
| 8,377,010 B2 | 2/2013 | Harding et al. |
| 8,382,741 B2 | 2/2013 | Chelak |
| 8,398,598 B2 | 3/2013 | Carlyon et al. |
| 8,398,607 B2 | 3/2013 | Fangrow, Jr. |
| 8,403,886 B2 | 3/2013 | Bialecki et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,164 B2 | 4/2013 | Fangrow |
| 8,409,165 B2 | 4/2013 | Niedospial, Jr. et al. |
| 8,414,542 B2 | 4/2013 | Stroup |
| 8,439,880 B2 | 5/2013 | Rondeau |
| 8,444,628 B2 | 5/2013 | Fangrow, Jr. |
| 8,454,579 B2 | 6/2013 | Fangrow, Jr. |
| 8,511,352 B2 | 8/2013 | Kraus et al. |
| 8,512,307 B2 | 8/2013 | Fangrow |
| 8,529,524 B2 | 9/2013 | Newton et al. |
| 8,540,692 B2 | 9/2013 | Fangrow |
| 8,551,037 B2 | 10/2013 | Suchecki et al. |
| 8,568,371 B2 | 10/2013 | Slopes et al. |
| 8,591,476 B2 | 11/2013 | Winsor et al. |
| 8,628,515 B2 | 1/2014 | Fangrow, Jr. et al. |
| 8,628,516 B2 | 1/2014 | Naftalovitz et al. |
| 8,636,720 B2 | 1/2014 | Truitt et al. |
| 8,640,725 B2 | 2/2014 | Truitt et al. |
| 8,671,964 B2 | 3/2014 | Py |
| 8,679,090 B2 | 3/2014 | Anderson et al. |
| 8,684,994 B2 | 4/2014 | Lev et al. |
| 8,701,696 B2 | 4/2014 | Guala |
| 8,702,675 B2 | 4/2014 | Imai |
| 8,715,222 B2 | 5/2014 | Truitt et al. |
| 8,715,247 B2 | 5/2014 | Mansour et al. |
| 8,721,627 B2 | 5/2014 | Albert |
| D707,355 S | 6/2014 | Bow |
| 8,747,370 B2 | 6/2014 | Feith et al. |
| 8,757,590 B2 | 6/2014 | Naftalovitz et al. |
| 8,758,306 B2 | 6/2014 | Lopez et al. |
| 8,801,678 B2 | 8/2014 | Panian et al. |
| 8,808,254 B2 | 8/2014 | Lynn |
| 8,814,849 B1 | 8/2014 | Winsor |
| 8,834,432 B2 | 9/2014 | Winsor et al. |
| 8,840,577 B1 | 9/2014 | Zollinger et al. |
| 8,864,725 B2 | 10/2014 | Ranalletta et al. |
| 8,870,846 B2 | 10/2014 | Davis et al. |
| 8,870,850 B2 | 10/2014 | Fangrow, Jr. |
| 8,876,784 B2 | 11/2014 | Cote, Sr. et al. |
| 8,882,742 B2 | 11/2014 | Dikeman et al. |
| 8,910,919 B2 | 12/2014 | Bonnal et al. |
| 8,945,084 B2 | 2/2015 | Warren et al. |
| 8,951,233 B2 | 2/2015 | Mansour |
| 8,968,261 B2 | 3/2015 | Kimball et al. |
| 8,968,271 B2 | 3/2015 | Guala |
| 8,974,425 B2 | 3/2015 | Tachizaki et al. |
| 8,974,433 B2 | 3/2015 | Fangrow |
| 8,979,804 B2 | 3/2015 | Ho et al. |
| 8,992,501 B2 | 3/2015 | Seifert et al. |
| 9,005,179 B2 | 4/2015 | Fangrow et al. |
| 9,005,180 B2 | 4/2015 | Seifert et al. |
| 9,017,295 B2 | 4/2015 | Pan |
| 9,032,997 B2 | 5/2015 | Abura et al. |
| 9,039,047 B2 | 5/2015 | Imai |
| 9,044,585 B2 | 6/2015 | Masuda et al. |
| 9,060,921 B2 | 6/2015 | Seifert et al. |
| 9,061,130 B2 | 6/2015 | Truitt et al. |
| 9,067,049 B2 | 6/2015 | Panian et al. |
| D734,456 S | 7/2015 | Cromett |
| 9,072,657 B2 | 7/2015 | Seifert et al. |
| 9,089,680 B2 | 7/2015 | Ueda et al. |
| 9,089,681 B2 | 7/2015 | Ueda et al. |
| 9,089,682 B2 | 7/2015 | Yeh et al. |
| D737,436 S | 8/2015 | Lev |
| 9,107,809 B2 | 8/2015 | Garfield et al. |
| 9,108,034 B2 | 8/2015 | Winsor |
| 9,114,244 B2 | 8/2015 | Yeh et al. |
| 9,119,950 B2 | 9/2015 | Mansour et al. |
| 9,138,572 B2 | 9/2015 | Zeytoonian et al. |
| 9,144,672 B2 | 9/2015 | Mansour et al. |
| 9,162,029 B2 | 10/2015 | Zollinger |
| 9,186,494 B2 | 11/2015 | Fangrow et al. |
| 9,192,753 B2 | 11/2015 | Lopez et al. |
| 9,198,831 B2 | 12/2015 | Rogers |
| 9,205,243 B2 | 12/2015 | Lopez et al. |
| 9,205,248 B2 | 12/2015 | Wu et al. |
| 9,212,772 B2 | 12/2015 | Ho et al. |
| 9,220,882 B2 | 12/2015 | Belley et al. |
| 9,234,616 B2 | 1/2016 | Carrez et al. |
| 9,238,128 B2 | 1/2016 | Yamaguchi et al. |
| 9,238,129 B2 | 1/2016 | Fangrow et al. |
| 9,259,565 B2 | 2/2016 | Siopes et al. |
| 9,278,205 B2 | 3/2016 | Quach et al. |
| 9,278,206 B2 | 3/2016 | Fangrow et al. |
| 9,289,588 B2 | 3/2016 | Chen |
| D753,283 S | 4/2016 | Efinger |
| 9,314,604 B2 | 4/2016 | Bonnal et al. |
| 9,345,641 B2 | 5/2016 | Kraus et al. |
| 9,352,086 B2 | 5/2016 | Guala |
| 9,366,371 B2 | 6/2016 | Naftalovitz et al. |
| 9,370,466 B2 | 6/2016 | Garfield et al. |
| 9,370,651 B2 | 6/2016 | Zollinger et al. |

(56) References Cited

U.S. PATENT DOCUMENTS

| | | |
|---|---|---|
| 9,375,559 B2 | 6/2016 | Feith et al. |
| 9,381,339 B2 | 7/2016 | Wu et al. |
| 9,393,398 B2 | 7/2016 | Truitt et al. |
| 9,409,007 B2 | 8/2016 | Yeh |
| 9,415,200 B2 | 8/2016 | Fangrow |
| 9,421,354 B2 | 8/2016 | Carmody et al. |
| 9,433,708 B2 | 9/2016 | Eddy |
| 9,440,060 B2 | 9/2016 | Fangrow |
| 9,533,137 B2 | 1/2017 | Fangrow |
| D786,427 S | 5/2017 | Nelson |
| D793,551 S | 8/2017 | Nelson |
| 9,750,926 B2 | 9/2017 | Lopez et al. |
| 9,884,176 B2 | 2/2018 | Fangrow et al. |
| D826,400 S | 8/2018 | Nelson |
| 10,086,188 B2 | 10/2018 | Fangrow |
| D838,842 S | 1/2019 | Shaw et al. |
| 10,195,413 B2 | 2/2019 | Lopez et al. |
| D849,939 S | 5/2019 | Nelson |
| 10,369,349 B2 | 8/2019 | Nelson |
| D890,335 S | 7/2020 | Nelson |
| 2001/0049508 A1 | 12/2001 | Fangrow, Jr. |
| 2002/0024036 A1 | 2/2002 | Rohrbough et al. |
| 2002/0120333 A1 | 8/2002 | Keogh et al. |
| 2002/0156430 A1 | 10/2002 | Haarala et al. |
| 2004/0006330 A1 | 1/2004 | Fangrow, Jr. |
| 2004/0201216 A1 | 10/2004 | Segal et al. |
| 2004/0221904 A1 | 11/2004 | Usher et al. |
| 2005/0010176 A1 | 1/2005 | Dikeman et al. |
| 2005/0020981 A1 | 1/2005 | Kurth |
| 2005/0059952 A1 | 3/2005 | Giuliano et al. |
| 2005/0121638 A1 | 6/2005 | Doyle |
| 2005/0124964 A1 | 6/2005 | Niedospial et al. |
| 2005/0212292 A1 | 9/2005 | Parrino et al. |
| 2005/0222541 A1 | 10/2005 | Lopez et al. |
| 2005/0234405 A1 | 10/2005 | Dikeman et al. |
| 2006/0004331 A1 | 1/2006 | Fangrow, Jr. |
| 2006/0161115 A1 | 7/2006 | Fangrow, Jr. |
| 2006/0200088 A1 | 9/2006 | Lopez |
| 2006/0200089 A1 | 9/2006 | Lopez et al. |
| 2006/0200090 A1 | 9/2006 | Lopez et al. |
| 2006/0206061 A1 | 9/2006 | Lopez et al. |
| 2006/0211997 A1 | 9/2006 | Fangrow, Jr. |
| 2006/0211998 A1 | 9/2006 | Fangrow, Jr. |
| 2006/0211999 A1 | 9/2006 | Fangrow, Jr. |
| 2006/0212001 A1 | 9/2006 | Fangrow, Jr. |
| 2006/0212003 A1 | 9/2006 | Fangrow, Jr. |
| 2006/0212006 A1 | 9/2006 | Fangrow, Jr. |
| 2006/0224127 A1 | 10/2006 | Fangrow, Jr. |
| 2006/0264842 A1 | 11/2006 | Fangrow, Jr. |
| 2006/0264844 A1 | 11/2006 | Fangrow, Jr. |
| 2006/0264849 A1 | 11/2006 | Lopez et al. |
| 2006/0264909 A1 | 11/2006 | Fangrow, Jr. |
| 2006/0264910 A1 | 11/2006 | Fangrow, Jr. |
| 2006/0270999 A1 | 11/2006 | Fangrow, Jr. |
| 2006/0271016 A1 | 11/2006 | Fangrow, Jr. |
| 2006/0276757 A1 | 12/2006 | Fangrow, Jr. |
| 2006/0276758 A1 | 12/2006 | Fangrow, Jr. |
| 2007/0100284 A1 | 5/2007 | Leinsing et al. |
| 2007/0106205 A1 | 5/2007 | Connell et al. |
| 2007/0112312 A1 | 5/2007 | Fangrow, Jr. |
| 2007/0112313 A1 | 5/2007 | Fangrow, Jr. |
| 2007/0224865 A1 | 9/2007 | Fangrow, Jr. |
| 2007/0225425 A1 | 9/2007 | Nash et al. |
| 2007/0235676 A1 | 10/2007 | Vangsness et al. |
| 2007/0254000 A1 | 11/2007 | Guo et al. |
| 2007/0270756 A1 | 11/2007 | Peppel et al. |
| 2008/0039802 A1 | 2/2008 | Vangsness et al. |
| 2008/0086095 A1 | 4/2008 | Dikeman et al. |
| 2008/0086097 A1 | 4/2008 | Rasmussen et al. |
| 2008/0086099 A1 | 4/2008 | McKinnon et al. |
| 2008/0097407 A1 | 4/2008 | Plishka |
| 2008/0169444 A1 | 7/2008 | Guala |
| 2008/0249508 A1 | 10/2008 | Lopez et al. |
| 2009/0005761 A1 | 1/2009 | Guala |
| 2009/0087606 A1 | 4/2009 | Julien |
| 2009/0198209 A1 | 8/2009 | Usher et al. |
| 2009/0209922 A1 | 8/2009 | Boisjoly |
| 2009/0292252 A1 | 11/2009 | Lareau et al. |
| 2009/0292274 A1 | 11/2009 | Guala |
| 2010/0030163 A1 | 2/2010 | Carrez et al. |
| 2010/0030164 A1 | 2/2010 | Kimball et al. |
| 2010/0036330 A1 | 2/2010 | Plishka et al. |
| 2010/0059474 A1 | 3/2010 | Brandenburger et al. |
| 2010/0059702 A1 | 3/2010 | Mansour et al. |
| 2010/0063456 A1 | 3/2010 | Rahimy et al. |
| 2010/0063482 A1 | 3/2010 | Mansour |
| 2010/0108681 A1 | 5/2010 | Jepson et al. |
| 2010/0152680 A1 | 6/2010 | Memahon |
| 2010/0174242 A1 | 7/2010 | Anderson et al. |
| 2010/0179514 A1 | 7/2010 | Guala |
| 2010/0241088 A1 | 9/2010 | Ranalletta et al. |
| 2010/0249723 A1 | 9/2010 | Fang, Jr. |
| 2010/0249724 A1 | 9/2010 | Cote, Sr. et al. |
| 2010/0249725 A1 | 9/2010 | Cote, Sr. et al. |
| 2010/0264343 A1 | 10/2010 | Jeory |
| 2010/0270792 A1 | 10/2010 | Lauer |
| 2010/0283238 A1 | 11/2010 | Deighan et al. |
| 2010/0292673 A1 | 11/2010 | Korogi et al. |
| 2010/0292674 A1 | 11/2010 | Jepson et al. |
| 2010/0300556 A1 | 12/2010 | Carmody et al. |
| 2010/0324502 A1 | 12/2010 | Guala |
| 2011/0004183 A1 | 1/2011 | Carrez et al. |
| 2011/0024664 A1 | 2/2011 | Bernard et al. |
| 2011/0028914 A1 | 2/2011 | Mansour et al. |
| 2011/0028915 A1 | 2/2011 | Siopes et al. |
| 2011/0046572 A1 | 2/2011 | Fangrow |
| 2011/0048540 A1 | 3/2011 | Stroup |
| 2011/0054440 A1 | 3/2011 | Lewis |
| 2011/0060293 A1 | 3/2011 | Guala |
| 2011/0087164 A1 | 4/2011 | Mosler et al. |
| 2011/0106046 A1 | 5/2011 | Hiranuma et al. |
| 2011/0125104 A1 | 5/2011 | Lynn |
| 2011/0130717 A1 | 6/2011 | David et al. |
| 2011/0130724 A1 | 6/2011 | Mansour et al. |
| 2011/0130726 A1 | 6/2011 | Crawford et al. |
| 2011/0130727 A1 | 6/2011 | Crawford et al. |
| 2011/0130728 A1 | 6/2011 | McKinnon |
| 2011/0152832 A1 | 6/2011 | Foshee et al. |
| 2011/0166532 A1 | 7/2011 | Brandenburger et al. |
| 2011/0178493 A1 | 7/2011 | Okiyama |
| 2011/0257590 A1 | 10/2011 | Winsor et al. |
| 2011/0264037 A1 | 10/2011 | Foshee et al. |
| 2011/0266477 A1 | 11/2011 | Stroup |
| 2011/0275988 A1 | 11/2011 | Davis et al. |
| 2011/0276010 A1 | 11/2011 | Davis et al. |
| 2011/0276031 A1 | 11/2011 | Hoang et al. |
| 2011/0295235 A1 | 12/2011 | Fangrow |
| 2011/0306940 A1 | 12/2011 | Miyasaka |
| 2011/0319821 A1 | 12/2011 | Kitani et al. |
| 2011/0319859 A1 | 12/2011 | Zeytoonian et al. |
| 2012/0013121 A1 | 1/2012 | Weckstrom |
| 2012/0022469 A1 | 1/2012 | Alpert |
| 2012/0042971 A1 | 2/2012 | Py |
| 2012/0046636 A1 | 2/2012 | Kriheli |
| 2012/0053529 A1 | 3/2012 | Imai |
| 2012/0059314 A1 | 3/2012 | Eichhorst |
| 2012/0059334 A1 | 3/2012 | Pan |
| 2012/0059346 A1 | 3/2012 | Sheppard et al. |
| 2012/0065626 A1 | 3/2012 | Naftalovitz et al. |
| 2012/0095407 A1 | 4/2012 | Chebator et al. |
| 2012/0109077 A1 | 5/2012 | Ryan |
| 2012/0130305 A1 | 5/2012 | Bonnal et al. |
| 2012/0130352 A1 | 5/2012 | Naftalovitz et al. |
| 2012/0150129 A1 | 6/2012 | Jin et al. |
| 2012/0153201 A1 | 6/2012 | Larose et al. |
| 2012/0157928 A1 | 6/2012 | Mermet |
| 2012/0157933 A1 | 6/2012 | Newton et al. |
| 2012/0179108 A1 | 7/2012 | Delabie |
| 2012/0192968 A1 | 8/2012 | Bonnal et al. |
| 2012/0209238 A1 | 8/2012 | Rosenquist et al. |
| 2012/0215182 A1 | 8/2012 | Mansour et al. |
| 2012/0220955 A1 | 8/2012 | Maseda et al. |
| 2012/0220977 A1 | 8/2012 | Yow |
| 2012/0220984 A1 | 8/2012 | Christensen et al. |

(56) References Cited

U.S. PATENT DOCUMENTS

| | | |
|---|---|---|
| 2012/0245564 A1 | 9/2012 | Tekeste et al. |
| 2012/0259292 A1 | 10/2012 | Koehler |
| 2012/0316514 A1 | 12/2012 | Mansour |
| 2012/0316536 A1 | 12/2012 | Carrez et al. |
| 2012/0323063 A1 | 12/2012 | Costanzo |
| 2012/0330277 A1 | 12/2012 | Winsor et al. |
| 2013/0012870 A1 | 1/2013 | Dikeman et al. |
| 2013/0030386 A1 | 1/2013 | Panian et al. |
| 2013/0035668 A1 | 2/2013 | Kitani et al. |
| 2013/0046315 A1 | 2/2013 | Woehr et al. |
| 2013/0053815 A1 | 2/2013 | Mucientes et al. |
| 2013/0060205 A1 | 3/2013 | Mansour et al. |
| 2013/0066293 A1 | 3/2013 | Garfield et al. |
| 2013/0079730 A1 | 3/2013 | Mosler et al. |
| 2013/0138075 A1 | 5/2013 | Lambert |
| 2013/0253478 A1 | 9/2013 | Fangrow, Jr. |
| 2013/0289534 A1 | 10/2013 | Fangrow, Jr. |
| 2013/0331800 A1 | 12/2013 | Newton et al. |
| 2014/0031765 A1 | 1/2014 | Siopes et al. |
| 2014/0104608 A1 | 4/2014 | Ozeki et al. |
| 2014/0135709 A1 | 5/2014 | Zollinger |
| 2014/0142519 A1 | 5/2014 | Truitt et al. |
| 2014/0155836 A1 | 6/2014 | Truitt et al. |
| 2014/0174578 A1 | 6/2014 | Bonnal et al. |
| 2014/0180219 A1 | 6/2014 | Ho et al. |
| 2014/0180258 A1 | 6/2014 | Ho et al. |
| 2014/0209197 A1 | 7/2014 | Carrez et al. |
| 2014/0257198 A1 | 9/2014 | Truitt et al. |
| 2014/0261860 A1 | 9/2014 | Heath et al. |
| 2014/0276455 A1 | 9/2014 | Yeh et al. |
| 2014/0276456 A1 | 9/2014 | Eddy |
| 2014/0276458 A1 | 9/2014 | Mansour et al. |
| 2014/0276459 A1 | 9/2014 | Yeh et al. |
| 2014/0276463 A1 | 9/2014 | Mansour et al. |
| 2014/0276466 A1 | 9/2014 | Yeh et al. |
| 2014/0296794 A1 | 10/2014 | Li |
| 2014/0303602 A1 | 10/2014 | Mansour et al. |
| 2014/0316350 A1 | 10/2014 | Yamaguchi et al. |
| 2014/0358033 A1 | 12/2014 | Lynn |
| 2014/0371686 A1 | 12/2014 | Sano et al. |
| 2015/0008664 A1 | 1/2015 | Tachizaki |
| 2015/0040987 A1 | 2/2015 | Reichert et al. |
| 2015/0040988 A1 | 2/2015 | Reichert et al. |
| 2015/0045746 A1 | 2/2015 | Macy, Jr. et al. |
| 2015/0045772 A1 | 2/2015 | Reichert et al. |
| 2015/0126942 A1 | 5/2015 | Lopez et al. |
| 2015/0148756 A1 | 5/2015 | Lynn |
| 2015/0151100 A1 | 6/2015 | Mansour |
| 2015/0157799 A1 | 6/2015 | Chen et al. |
| 2015/0157800 A1 | 6/2015 | Chen et al. |
| 2015/0157848 A1 | 6/2015 | Wu et al. |
| 2015/0176715 A1 | 6/2015 | Huang et al. |
| 2015/0190627 A1 | 7/2015 | Ueda et al. |
| 2015/0196749 A1 | 7/2015 | Ziv et al. |
| 2015/0196750 A1 | 7/2015 | Ueda et al. |
| 2015/0202424 A1 | 7/2015 | Harton |
| 2015/0258325 A1 | 9/2015 | Panian et al. |
| 2015/0265827 A1 | 9/2015 | Keyser et al. |
| 2015/0265829 A1 | 9/2015 | Truitt et al. |
| 2015/0297817 A1 | 10/2015 | Guala |
| 2015/0297880 A1 | 10/2015 | Ogawa et al. |
| 2015/0313523 A1 | 11/2015 | Chelak et al. |
| 2015/0320992 A1 | 11/2015 | Bonnet et al. |
| 2015/0374910 A1 | 12/2015 | Mansour |
| 2016/0000364 A1 | 1/2016 | Mendels et al. |
| 2016/0001057 A1 | 1/2016 | Lopez et al. |
| 2016/0015958 A1 | 1/2016 | Ueda et al. |
| 2016/0015960 A1 | 1/2016 | Bonnal |
| 2016/0015961 A1 | 1/2016 | Mansour et al. |
| 2016/0022977 A1 | 1/2016 | Ueda et al. |
| 2016/0022978 A1 | 1/2016 | Ueda |
| 2016/0030730 A1 | 2/2016 | Mosier et al. |
| 2016/0038730 A1 | 2/2016 | Zollinger |
| 2016/0089492 A1 | 3/2016 | Burnard et al. |
| 2016/0089529 A1 | 3/2016 | Bolz et al. |
| 2016/0106970 A1 | 4/2016 | Fangrow |
| 2016/0114147 A1 | 4/2016 | Siopes et al. |
| 2016/0129235 A1 | 5/2016 | Ryan |
| 2016/0136051 A1 | 5/2016 | Lavi |
| 2016/0144110 A1 | 5/2016 | Ueda |
| 2016/0158524 A1 | 6/2016 | Quach et al. |
| 2016/0199575 A1 | 7/2016 | Belley et al. |
| 2016/0235961 A1 | 8/2016 | Maffei |
| 2016/0263369 A1 | 9/2016 | Naftalovitz et al. |
| 2016/0279404 A1 | 9/2016 | Nelson |
| 2016/0317798 A1 | 11/2016 | Lopez et al. |
| 2017/0128710 A1 | 5/2017 | Fangrow |
| 2018/0289942 A1 | 1/2018 | Fangrow |
| 2018/0099137 A1 | 4/2018 | Fangrow |
| 2019/0001114 A1 | 1/2019 | Fangrow |
| 2019/0113166 A1 | 4/2019 | Zoellner et al. |

FOREIGN PATENT DOCUMENTS

| | | |
|---|---|---|
| CA | 2 175 021 | 11/1996 |
| CH | 636526 | 6/1983 |
| CH | 670955 | 7/1989 |
| DE | 855 319 | 9/1952 |
| DE | 84 25 197.2 | 9/1985 |
| DE | 37 40 269 | 6/1989 |
| EP | 0 263 789 | 4/1988 |
| EP | 0 309 771 | 4/1989 |
| EP | 0 399 119 | 11/1990 |
| EP | 0 446 463 | 9/1991 |
| EP | 0 805 930 | 6/2002 |
| EP | 1 466 644 | 10/2004 |
| EP | 1 547 646 | 6/2005 |
| EP | 1 563 867 | 8/2005 |
| EP | 1 854 502 | 11/2007 |
| EP | 1 857 137 | 11/2007 |
| EP | 1 669 101 | 7/2008 |
| EP | 2 004 274 | 12/2008 |
| FR | 2 707 505 | 1/1995 |
| GB | 2 000 685 | 1/1979 |
| GB | 2 001 146 | 1/1979 |
| GB | 2034 185 | 6/1980 |
| JP | 2006-43354 | 2/2006 |
| JP | 2009-299871 | 12/2009 |
| NZ | 333508 A | 8/2005 |
| WO | WO 1992/20736 | 11/1992 |
| WO | WO 1994/22523 | 10/1994 |
| WO | WO 1996/23158 | 1/1996 |
| WO | WO 1999/59672 | 11/1999 |
| WO | WO 1999/61093 | 12/1999 |
| WO | WO 2000/20070 | 4/2000 |
| WO | WO 2003/018104 | 3/2003 |
| WO | WO 2003/086529 | 10/2003 |
| WO | WO 2005/115521 | 8/2005 |
| WO | WO 2006/013433 | 2/2006 |
| WO | WO 2006/062912 | 6/2006 |
| WO | WO 2007/112278 | 10/2007 |
| WO | WO 2008/048777 | 4/2008 |
| WO | WO 2008/062741 | 5/2008 |
| WO | WO 2009/052433 | 4/2009 |
| WO | WO 2009/111596 | 9/2009 |
| WO | WO 2010/004471 | 1/2010 |
| WO | WO 2010/135080 | 11/2010 |
| WO | WO 2011/064738 | 6/2011 |

OTHER PUBLICATIONS

U.S. Appl. No. 29/510,851, filed Dec. 3, 2014, Nelson.
U.S. Appl. No. 29/510,852, filed Dec. 3, 2014, Nelson.
U.S. Appl. No. 29/603,008, filed May 5, 2017, Nelson.
U.S. Appl. No. 14/961,163, filed Dec. 7, 2015, Lopez et al.
U.S. Appl. No. 29/611,987, filed Jul. 27, 2017, Nelson.
"Faulding Inc. receives FDA permission to market patented Safe-Connect Valve", dated Dec. 2, 1996.
BD Medical: Needleless IV Access Devices, one page, 2007.
Capless BackcheckValve, dated Sep. 3, 1993.
CardinalHealth, SmartSite Brochure: "SmartSite® Disposables," 2004, in 12 pages.

(56) References Cited

OTHER PUBLICATIONS

Carefusion, Medegen Introduces MaxPlus® Clear, First and Only Clear Positive Displacement Connector for Use in Infusion Therapy, MaxGuard News, one page article, dated Mar. 10, 2008—Ontario, CA.
Caresite™ Luer Access Device, dated 2010.
Clearlink, needleless IV access system, Baxter 2007 brochure in 2 pages.
F.D.A. 510(k) Summary of Safety and Effectiveness, dated Nov. 17, 1997.
LifeShield TKO Anti-Reflux Device Brochure, appears to contain a date of Feb. 2008.
MEDI-4955 Liquid Silicone Rubber from NuSil Silicone Technology, dated Dec. 17, 2010.
MicroClave Connector Brochure. The MicroClave was available before Mar. 25, 2008.
MicroClave Neutral Displacement Connector A Needlefree Closed System Device. Brochure Sep. 24, 2008.
MicroClave Product Page Video Shots. Sep. 24, 2008.
Nexus Medical Nexus TKO, appears to contain a date of Mar. 2006.
PASV Valve Connector Brochure, which appears to be at least as early as Feb. 20, 2001.
Saechtling Tworzywa Sztuczne, WN-T Warszawa, 1999, V edition, pp. 224-225.

\* cited by examiner

CHECK VALVE

RELATED APPLICATIONS

This application is a continuation of U.S. application Ser. No. 15/179,760, filed Jun. 10, 2016, titled MEDICAL FLUID MANIFOLD, which is a continuation of PCT/US2014/068455, filed Dec. 3, 2014, titled CHECK VALVE, which claims the benefit of U.S. Provisional Application No. 61/914,892, filed Dec. 11, 2013, titled CHECK VALVE, the entire contents of each are incorporated by reference herein and made a part of this specification.

BACKGROUND

Field of the Disclosure

A variety of devices and techniques exist for the manipulation of fluids in hospitals and medical settings, and in particular the selective facilitation of fluid movement to or from patients or to or from a fluid flow line. Fluid flow lines rely on a variety of connectors to help develop preferred flow characteristics or access points. Many connectors include check valves.

Description of the Related Art

Current fluid flow systems, medical connectors, and check valves have various limitations and disadvantages and a need exists for further improvement.

SUMMARY OF THE DISCLOSURE

A variety of fluid flow lines and systems are used in hospitals and medical settings for the selective facilitation of fluid movement to or from patients. For example, central venous catheters can be used to administer IV fluids, various medications or blood products, and/or parenteral nutrition. In some embodiments, medical connectors can be provided on one end of a flow line to allow for periodic access to a flow line or for application of different inputs to the flow line. Generally, these structures require valves to allow fluid to enter the main flow line while preventing retrograde flow.

In certain situations, it may be desirable to provide multiple connections to a flow line into a patient's blood stream. This can allow for easy connection to multiple fluid or medication sources. This is particularly useful in treatments that require multiple inputs, such as chemotherapy. When multiple connections are desired, a manifold, extension set, or other multi-input structure can be used. These structures also require valves to allow fluid to enter the main flow line but that preferably prevent retrograde flow. In various embodiments described herein, such valves can be designed to maximize efficiency and desired flow rates and flow characteristics while still providing a check on retrograde flow. In some situations, it may be desirable to provide a single connection point with one way flow.

In various embodiments, a medical check valve for use in a medical device to provide one-way fluid flow between a first fluid location and a second fluid location can include a flexible diaphragm having a top surface, a bottom surface, and a side wall between the top surface and the bottom surface, and a first support member extending from the bottom surface of the flexible diaphragm and a second support member extending from the bottom surface of the flexible diaphragm, the first support member and second support member positioned to define a line of or axis of symmetry that bisects the bottom surface without passing through the first support member or the second support member. The flexible diaphragm can have a first position in which the top surface is generally planar and is configured to seal against a fluid opening and a second position in which the top surface of the diaphragm is curved generally around the line of symmetry and is configured to be displaced from the fluid opening.

In some embodiments, the line of symmetry can be the only line of symmetry that bisects the bottom surface without passing through the first support member or the second support member. In some embodiments, the flexible diaphragm can be a disc. In some embodiments, the support members can be positioned 180 degrees apart about the disc. In some embodiments, the flexible diaphragm can be non-perforate. In some embodiments, the flexible diaphragm, the first support member, and the second support member can be integrally formed and/or molded into a single unitary piece.

In some embodiments, the diaphragm can be configured to move from the first position to the second position at varying amounts of pressure. For example, in some embodiments a net pressure of less than 3 psi on the top surface of the flexible diaphragm is sufficient to move the diaphragm from the first position to the second position. In some embodiments, a net pressure of less than 1 psi on the top surface of the flexible diaphragm is sufficient to move the diaphragm from the first position to the second position. In some embodiments, a positive net pressure on the bottom surface of the flexible diaphragm is needed to maintain the flexible diaphragm in the first position.

In various embodiments, a medical manifold for use in providing access to a fluid flow path can include a housing having a first port, a second port, a first channel connecting the first port and the second port and defining a first flow path, and a third port having a recess in an outer wall of the housing and a second channel fluidly connecting the recess and the first flow path. The manifold can also include a valve member having a diaphragm and a plurality of support members configured to be positioned in the recess to thereby define a space between a bottom wall of the recess and the diaphragm. The manifold can also include a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path.

In some embodiments, an outer wall of the recess can be cylindrical. In some embodiments, an outer wall of the recess can include multiple walls. In some embodiments, the third port can have at least two projections extending from the bottom wall of the recess and adjacent the second channel, wherein the projections define an outer channel between the projections and an outer wall of the recess and at least two transverse channels between the projections. In some embodiments, the plurality of support members can be configured to be positioned on at least two of the projections. In such embodiments, the valve member in an open position is configured to allow fluid to flow from the medical connector, past the valve member to the outer channel, through the transverse channels, and into the second channel.

In some embodiments, the valve member can be biased toward the closed position. In some embodiments, the valve member can be configured to move from the closed to the open position as a result of pressure from fluid in the medical connector. In some embodiments, the housing can be monolithic. In some embodiments, a net pressure of less than 3 psi on the valve member can be sufficient to move the valve member from the closed position to the open position.

In various embodiments, a medical manifold for use in providing access to a fluid flow path can include a first port, a second port, a first channel connecting the first port and the second port and defining a first flow path, and a housing having a third port in an outer wall of the housing and a second channel fluidly connecting the third port and the first flow path. The manifold can also include a valve member having a diaphragm and a plurality of support members configured to be positioned in the third port to thereby define a space between a bottom wall of the third port and the diaphragm. The manifold can also include a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path.

In some embodiments, the third port further includes at least two projections extending from the bottom wall of the third port and adjacent the second channel, wherein the projections define at least two transverse channels between the projections. The plurality of support members may be configured to be positioned on at least two of the projections. In some embodiments, the third port of the medical manifold includes a recess and the projections extend from the bottom wall of the recess. A wall surrounding the recess may extend outward from the housing and a portion of the medical connector may be configured to surround at least a portion of the wall. In some embodiments, the medical connector is sonically welded to the third port.

In some embodiments, an outer wall of the third port can be cylindrical. In some embodiments, an outer wall of the third port can include multiple walls. In some embodiments, the third port can have at least two projections extending from the bottom wall of the third port and adjacent the second channel, wherein the projections define an outer channel between the projections and an outer wall of the third port and at least two transverse channels between the projections. In some embodiments, the plurality of support members can be configured to be positioned on at least two of the projections. In such embodiments, the valve member in an open position is configured to allow fluid to flow from the medical connector, past the valve member to the outer channel, through the transverse channels, and into the second channel.

In various embodiments, a medical manifold for use in providing access to a fluid flow path can include a first port, a second port, a first channel connecting the first port and the second port and defining a first flow path, and a housing having a third port in an outer wall of the housing and a second channel fluidly connecting the third port and the first flow path. The manifold can also include a valve member having a diaphragm and a plurality of support members configured to be positioned in the third port to thereby define a space between a bottom wall of the third port and the diaphragm. The manifold can also include a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path. The medical manifold can also include a second housing including a fourth port with a third channel fluidly connecting the fourth port and the first flow path. In some embodiments, the manifold can include a second valve member with a diaphragm and a plurality of support members configured to be positioned in the fourth port to thereby define a space between a bottom wall of the fourth port and the diaphragm. Some manifolds can include a second medical connector configured to attach to the fourth port, wherein the second valve member in a closed position is configured to seal against an opening into the second medical connector and the second valve member in an open position is configured to allow fluid to flow from the second medical connector, past the second valve member, through the third channel, and into the first flow path. In some embodiments, the first and second housings are monolithic while in other embodiments, wherein the first and second housings are joined by a flexible connecting element.

DETAILED DESCRIPTION OF THE PREFERRED EMBODIMENTS

With reference to the attached figures, certain embodiments and examples of fluid flow systems, medical connectors, and valves will now be described. Various embodiments of check valves described herein are with reference to a manifold or extension set, but they are not so limited. In some aspects, they can be applied to any system to provide for one-way flow between a medical connector and a fluid flow line, such as in, for example, IV sets, stopcocks or other branched connectors including y-site connectors, and other systems. As used herein, the term "fluid" refers to either gases or liquids.

Figure 1:
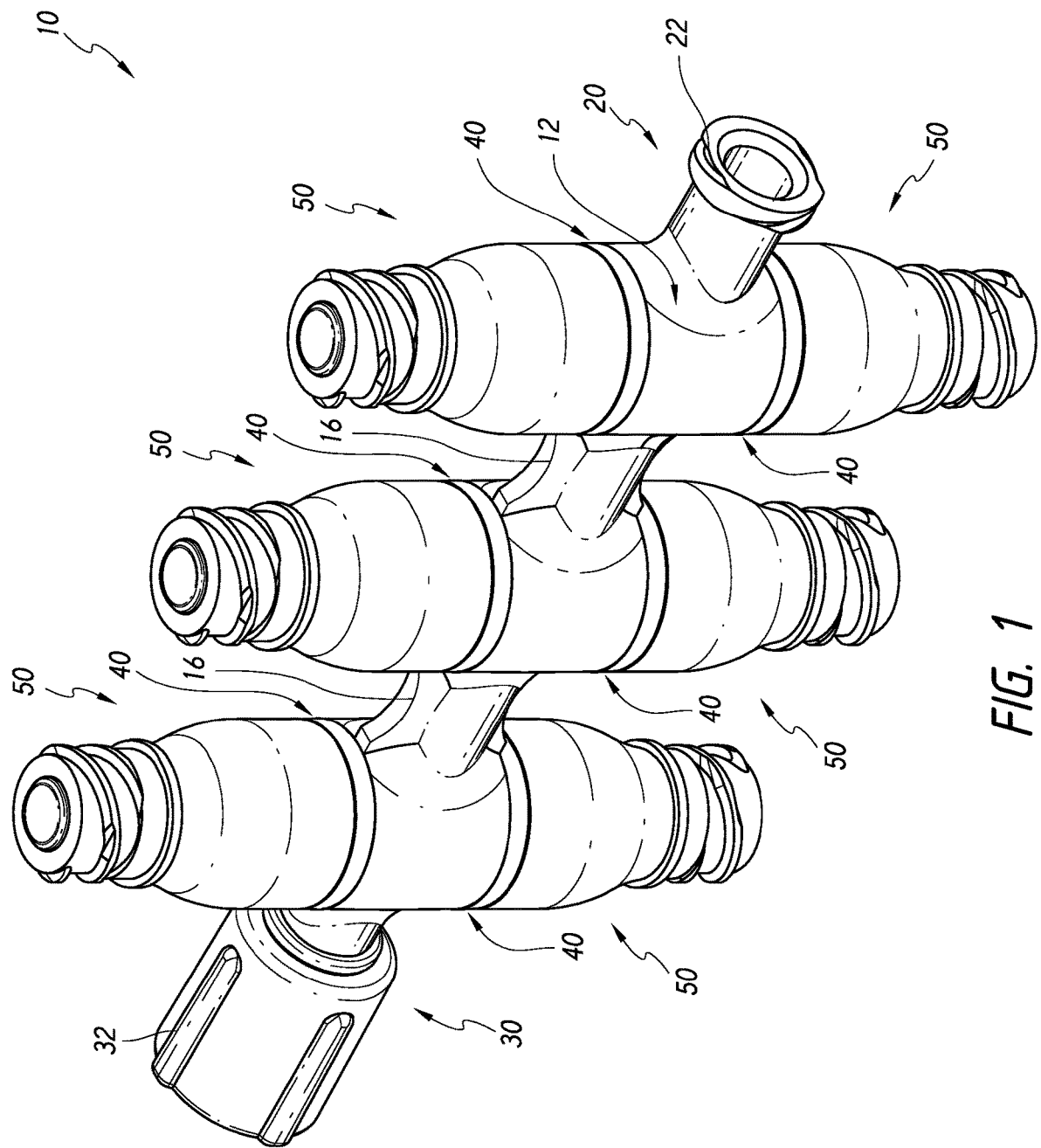
FIG. 1 is a perspective view of one embodiment of a manifold.

FIG. 1 illustrates an embodiment of a manifold 10 that can be used to provide access to a fluid flow path. The manifold can include a manifold housing 12 that can include a first port 20 and a second port 30. In some embodiments, the housing can be one integral piece, and in some embodiments it can include multiple pieces such that the manifold includes first and second ports connected by a fluid path, but the ports are connected by separately formed units, for example tubes, to the housing. In some embodiments, multiple housings may be connected between the first and second ports. Preferably, even when connected by flexible joints, the manifold in a resting position defines a generally linear fluid path between the first and second ports with one or more ports branching off that path. In some embodiments, those one or more ports branch off at about 90 degrees from the flow path between the first and second ports. The manifold can be inserted into a fluid flow line with the first port 20 configured to attach to one end of the line and the second port 30 configured to attach to a second end of the line. The ports can be configured to accommodate any standard medical connector or implement, and can be adapted to conform with ANSI (American National Standards Institute) or other applicable standards. In some embodiments, different ports can also be configured to have nonstandard connections.

In some embodiments, a first port 20 can have a threaded end 22 that can be used to connect to a threaded medical connector. In some embodiments, a second port 30 can have a male luer lock 32, including a tapered cannula 34 (visible in FIGS. 3 and 4).

In some embodiments, the manifold 10 can include a plurality of access ports 40, described and illustrated in more detail below. The access ports can be adapted to connect or attach to a variety of types of medical connectors 50. In some embodiments, as illustrated, a medical connector 50 can be a needleless connector. In the illustrated embodiment, the manifold includes six medical connectors 50, three on a first side of the manifold and three on a second side of the manifold.

Figure 2:
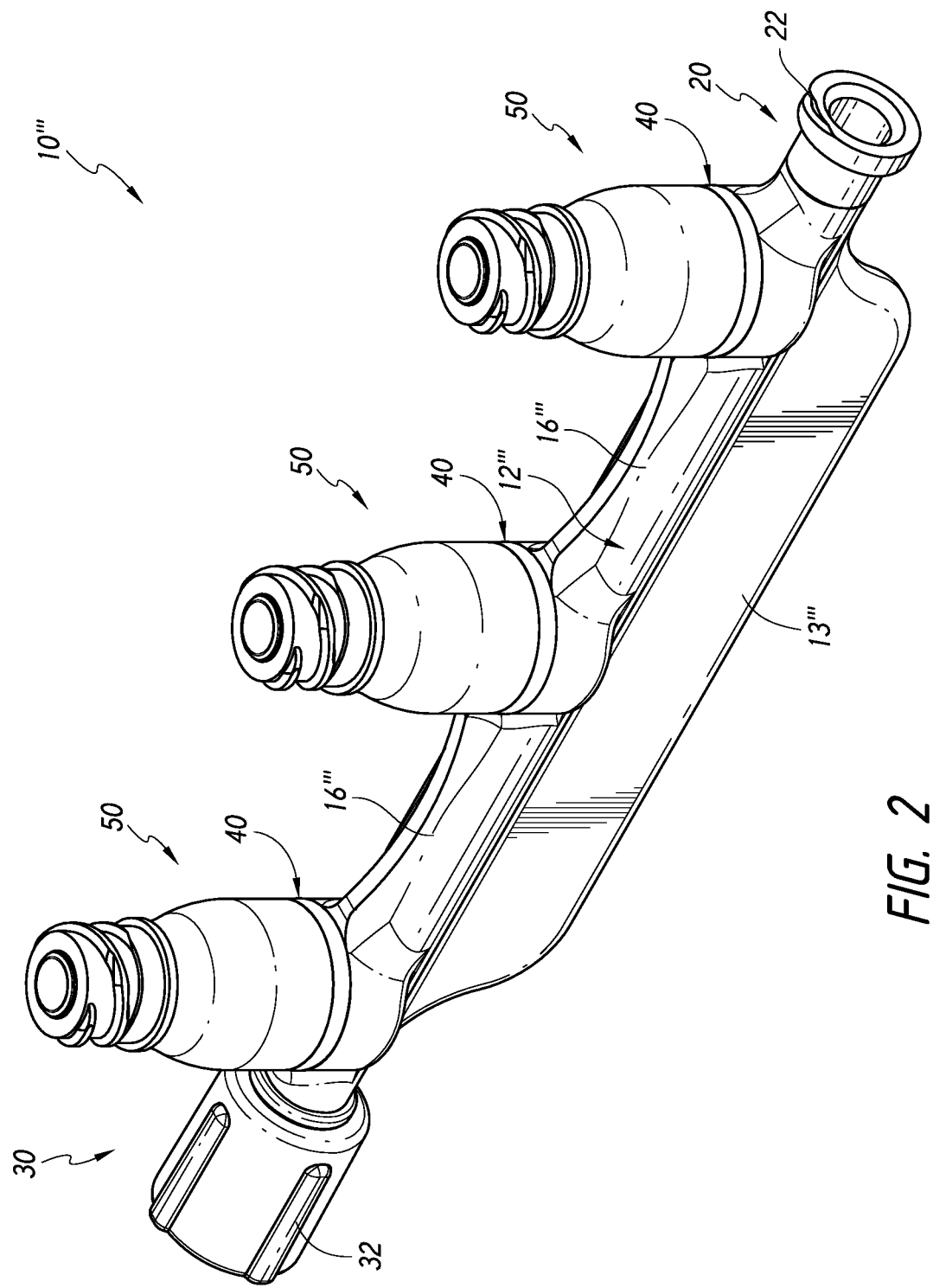
FIG. 2 is a perspective view of one embodiment of a manifold.
Figure 2A:
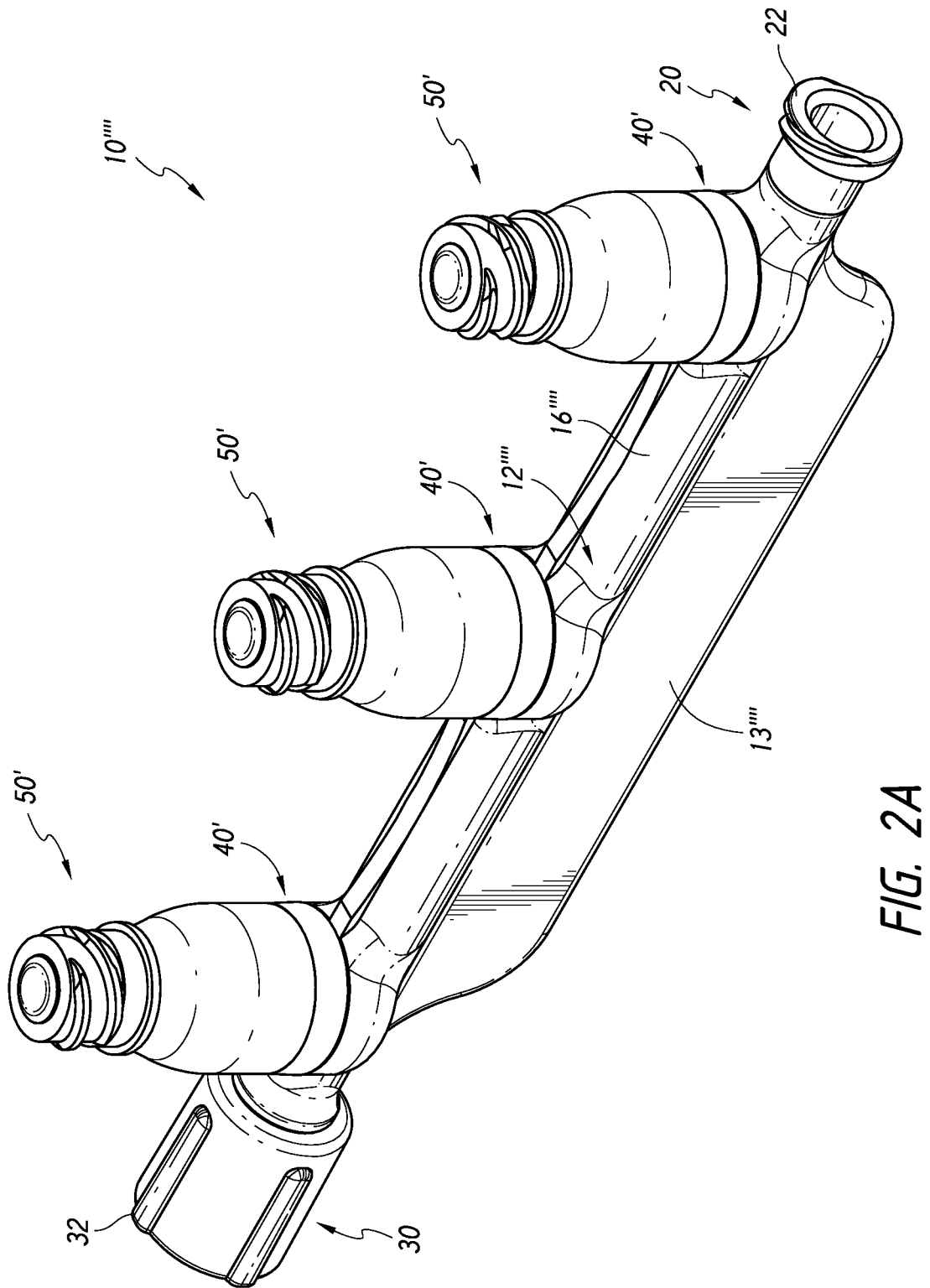
FIG. 2A is a perspective view of an embodiment of a manifold with a modified projection attachment.

In various embodiments, a manifold can have varying numbers of access ports and medical connectors. For example, FIG. 2 illustrates an embodiment of a manifold 10''' that has three access ports and medical connectors 50 on one side of the manifold. Housing 12''' includes joints 16''' and can include an extended portion or fin 13 that may be positioned on the side opposite the medical connectors. Fin 13''' can be provided to add stability to the manifold 10''' and may be configured to facilitate the handling or control by a nurse or other user of the manifold 10''' during use or to attach the manifold 10' to a convenient resting place. FIG. 2A shows an alternative manifold 10'''' also including three access ports and medical connectors 50' on one side. Housing 12'''' includes joints 16'''' and can include an extended portion or fin 13'''' that may be positioned on the side opposite the medical connectors. Fin 13'''' can be provided to add stability to the manifold 10'''' and may be configured to facilitate the handling or control by a nurse or other user of the manifold 10'''' during use or to attach the manifold 10'''' to a convenient resting place. As shown, joints 16''' may include shallow curved portions as compared to the curved portions on joints 16''' shown in FIG. 2. Curved portions and other structures can be used to change the strength of the housing and to provide a convenient place to hold the manifold.

Figure 1A:
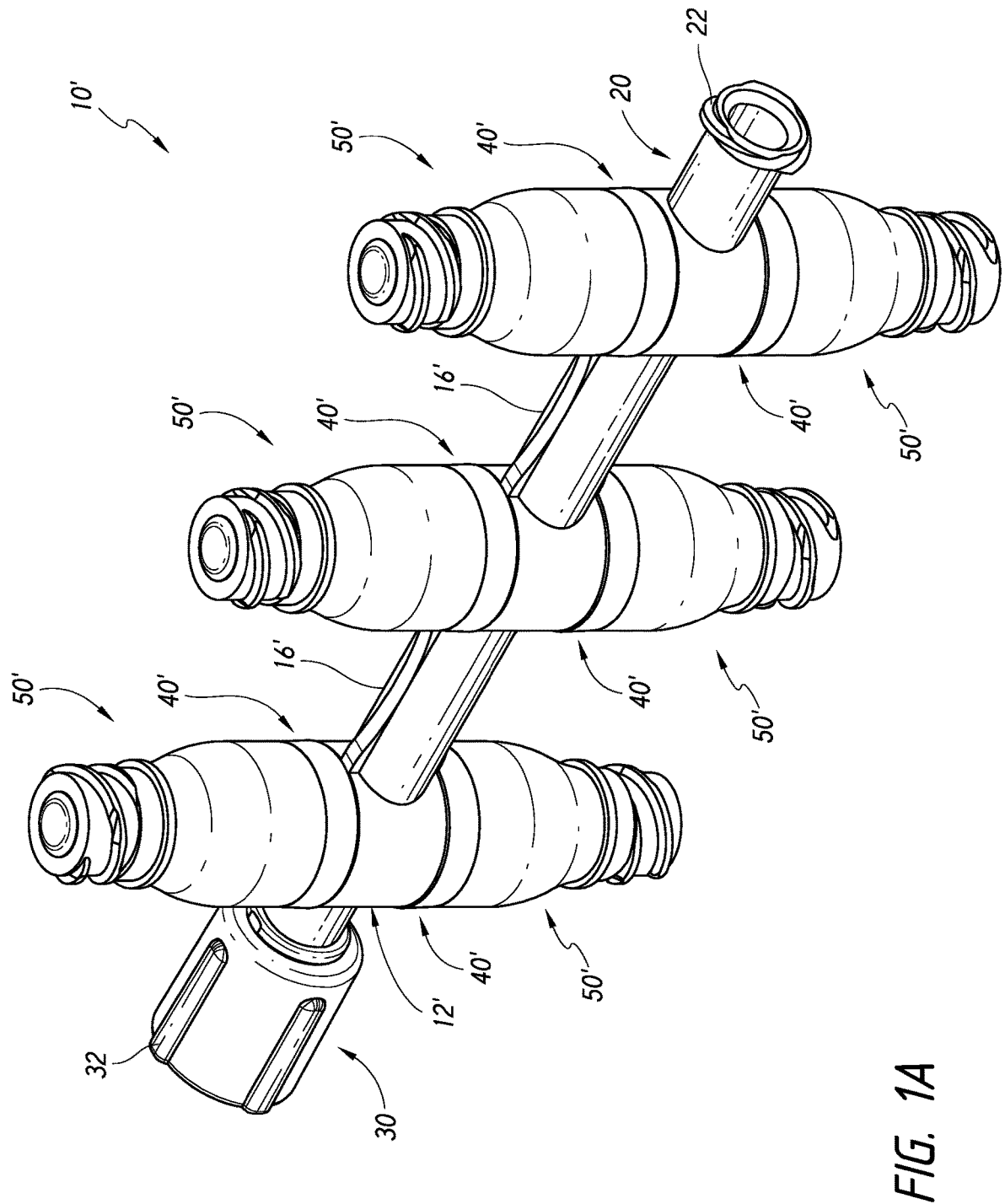
FIG. 1A is a perspective view of an embodiment of a manifold with a modified projection attachment.
Figure 1B:
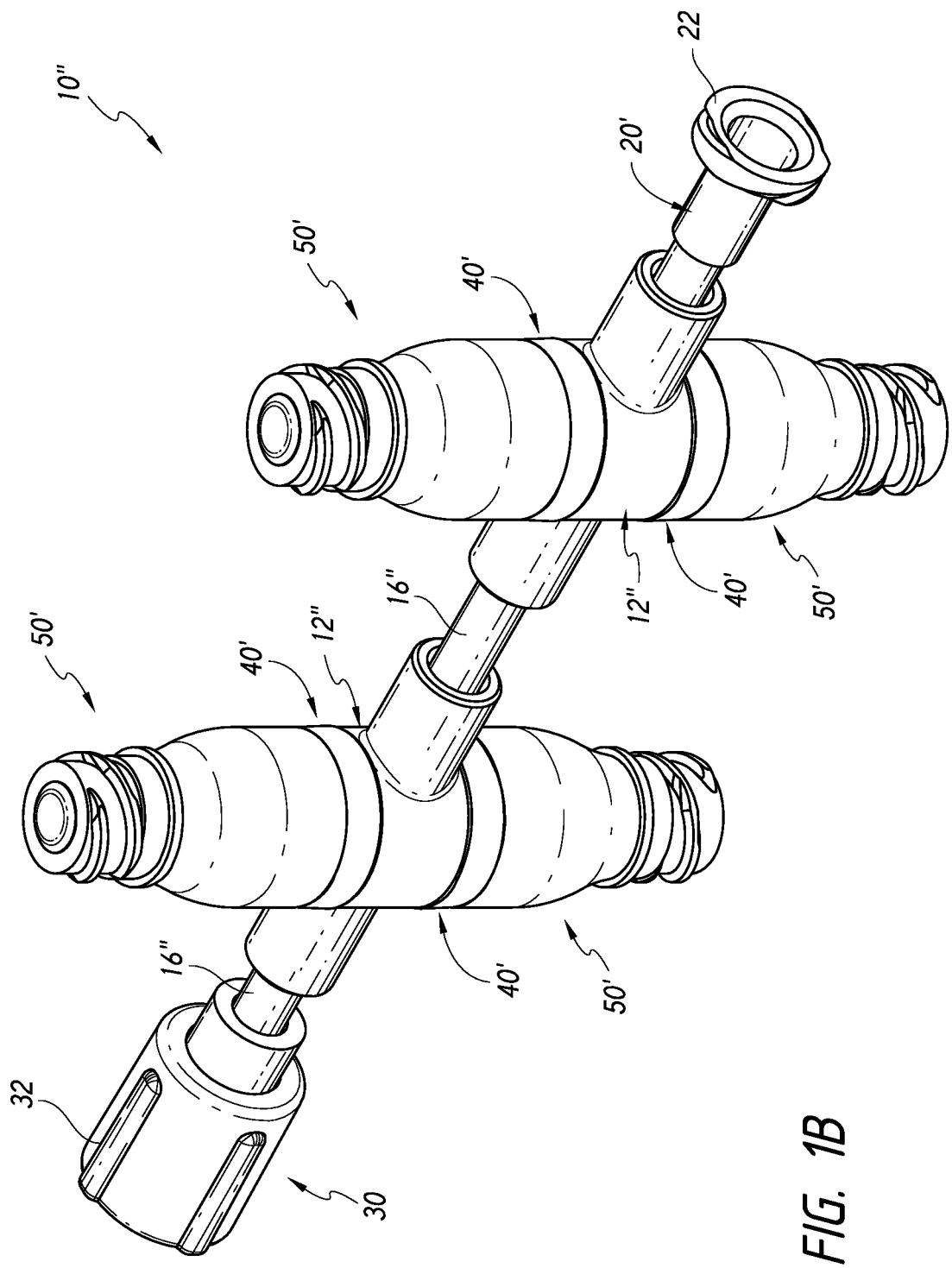
FIG. 1B is a perspective view of an embodiment of a manifold component.
Figure 2B:
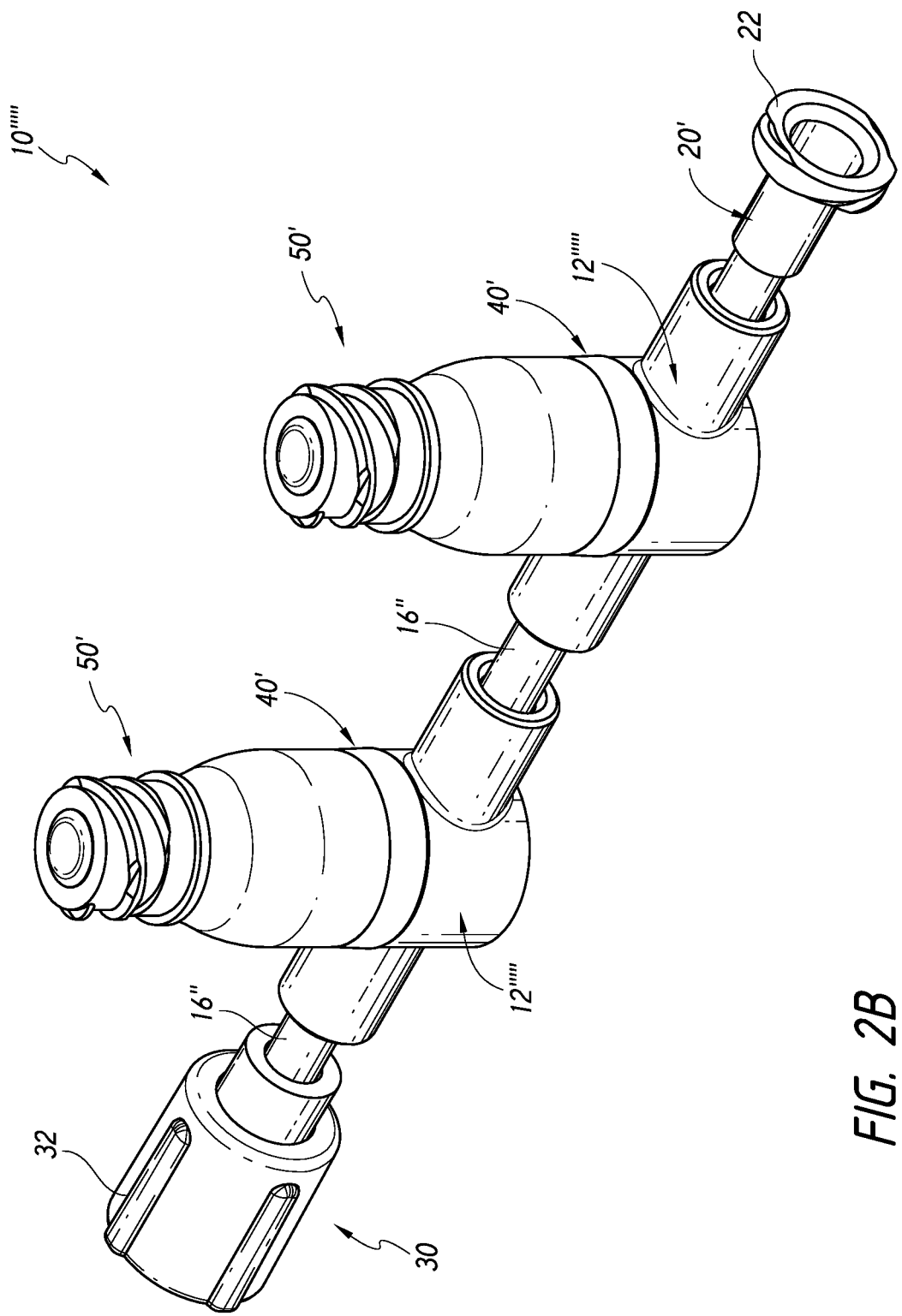
FIG. 2B is a perspective view of an embodiment of a manifold component.

Other combinations of ports are also possible. For example, FIG. 1B shows a manifold 10'' including two double housings 12''. FIG. 2B shows a manifold 10''''' including two single housings 12'''''. As discussed above, a single manifold may include various combinations of such housings as desired.

Embodiments of the invention may provide various ways to connect medical connectors to the housing ports, as discussed in greater detail below. For example, FIG. 1A shows a six port manifold 10' with alternative ports 40' and modified connectors 50'.

As shown, in some embodiments various modifications can be made to the connecting portions or joints 16 between the ports. For example, FIG. 1 shows a first version of the joints 16 while FIG. 1A shows an alternative joint 16' that includes shallow arched or curved portions. As shown in FIG. 1B, in some embodiments, rather than having a single housing 12 (see, for example, FIGS. 1 and 1A), a manifold 10'' can have a plurality of housings 12'' joined by a flexible connecting portion, for example, tubing. Thus, for example, in some embodiments the joints 16'' of the manifolds that connect housings having medical connectors or pairs of medical connectors can be formed of tubing.

FIG. 1B shows two double housings 12''. Various combinations are also possible. In some embodiments, a single housing 12'' with double ports may be provided and can be accessed by first and second ports 20' and 30. First port 20' may be similar to first port 20, except the rigid portion may be longer to accommodate the appropriate section of a medical implement, for example, a male luer. In some embodiments, the manifold may include 3 or more housings 12'' with corresponding medical connectors. Accordingly, the manifold can readily customized to provide an appropriate solution according to a user's needs. In addition, the manifold may include a combination of housings and ports, for example, a manifold may be provided with one or more double housing 12'' and one or more single housings 12''''' (see FIG. 2B). Providing flexible joints allows the manifold to flex and adapt to the needs of the user. For example, a port may be rotated to ease access while minimizing the movement of other ports that may already be accessed by various medical devices. The flexible joints of the manifold are permanently attached, for example by bonding or glueing, to their respective housings and ports such that the manifold is a single unity.

In some embodiments, various ports may remain connected or unconnected to one or more fluid sources and/or to a patient. For example, in some embodiments, one of the first port 20 and second port 30 can be connected to a patient, the other of the first port and second port may be sealed (such as with a medical connector 50 or a similar sealed access port) and unconnected to a fluid source, and one or more of the medical connectors 50 can be connected to a fluid source for the patient. In some embodiments, embodiments of the manifold can be used without a patient, for example, to combine one or more fluids into a single fluid receptacle (not shown). Accordingly, embodiments of the invention need not be used in direct connection with a patient.

Figure 3:
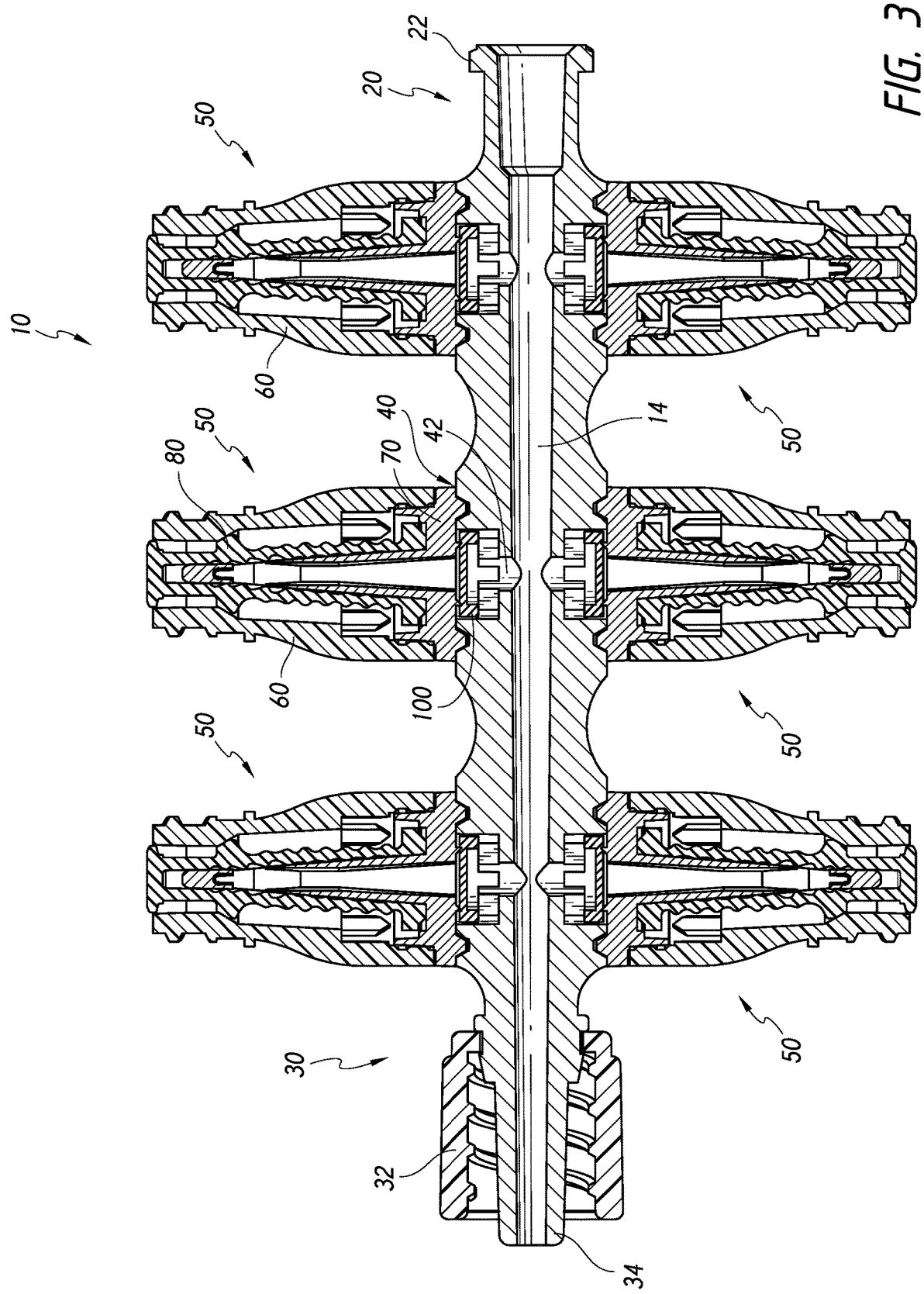
FIG. 3 is a cross-sectional view of the manifold of FIG. 1.
Figure 4:
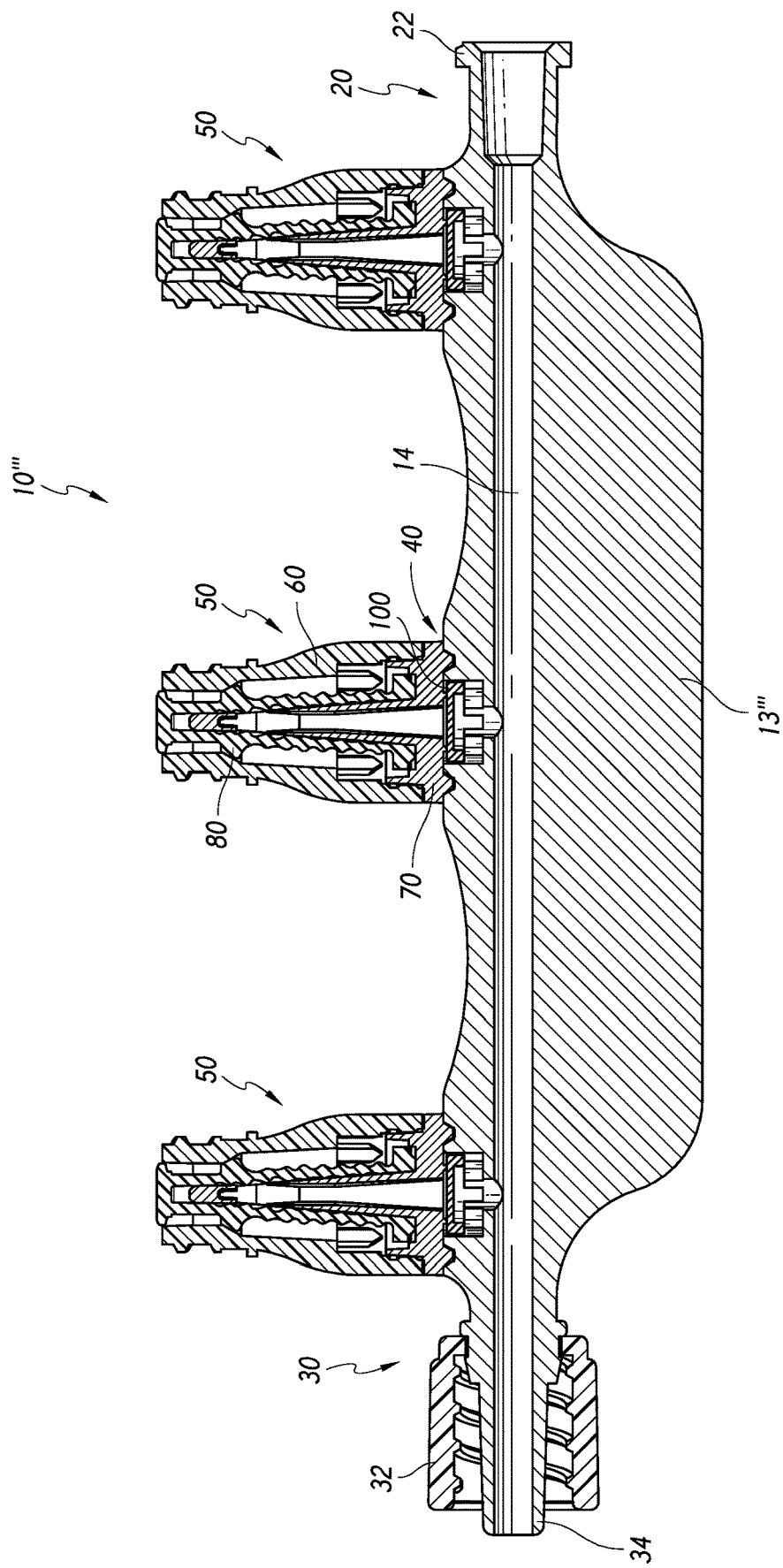
FIG. 4 is a cross-sectional view of the manifold of FIG. 2.

FIGS. 3 and 4 illustrate cross-sectional views of the manifolds of FIGS. 1 and 2, respectively. As illustrated, medical connectors 50 can attach to the manifold at access ports 40. In some embodiments, a medical connector 50 can be a needleless medical connector that includes a connector body 60, a connector base 70, and a connector valve member 80 positioned at least partially within the connector body 60. Further details regarding needless medical connectors that can be used are found in U.S. Provisional Patent Application No. 61/914,680, filed Dec. 11, 2013, the entire contents of which are hereby incorporated by reference herein and are included as an appendix to this application.

In some embodiments, other types of medical connectors or of needleless medical connectors can be attached to the access ports 40 of the manifolds. These can include connectors configured to receive syringes and connectors of varying designs. In some embodiments, a manifold can include one or more of a first type of medical connector and one or more of a second type of medical connector. In some embodiments, a manifold can include more than two types of medical connectors. In some embodiments, first port 20 and/or second port 30 may include sealed access ports that are similar to those that may be used for access ports 40. Similarly, they can include check valves such as those described herein.

Figure 3A:
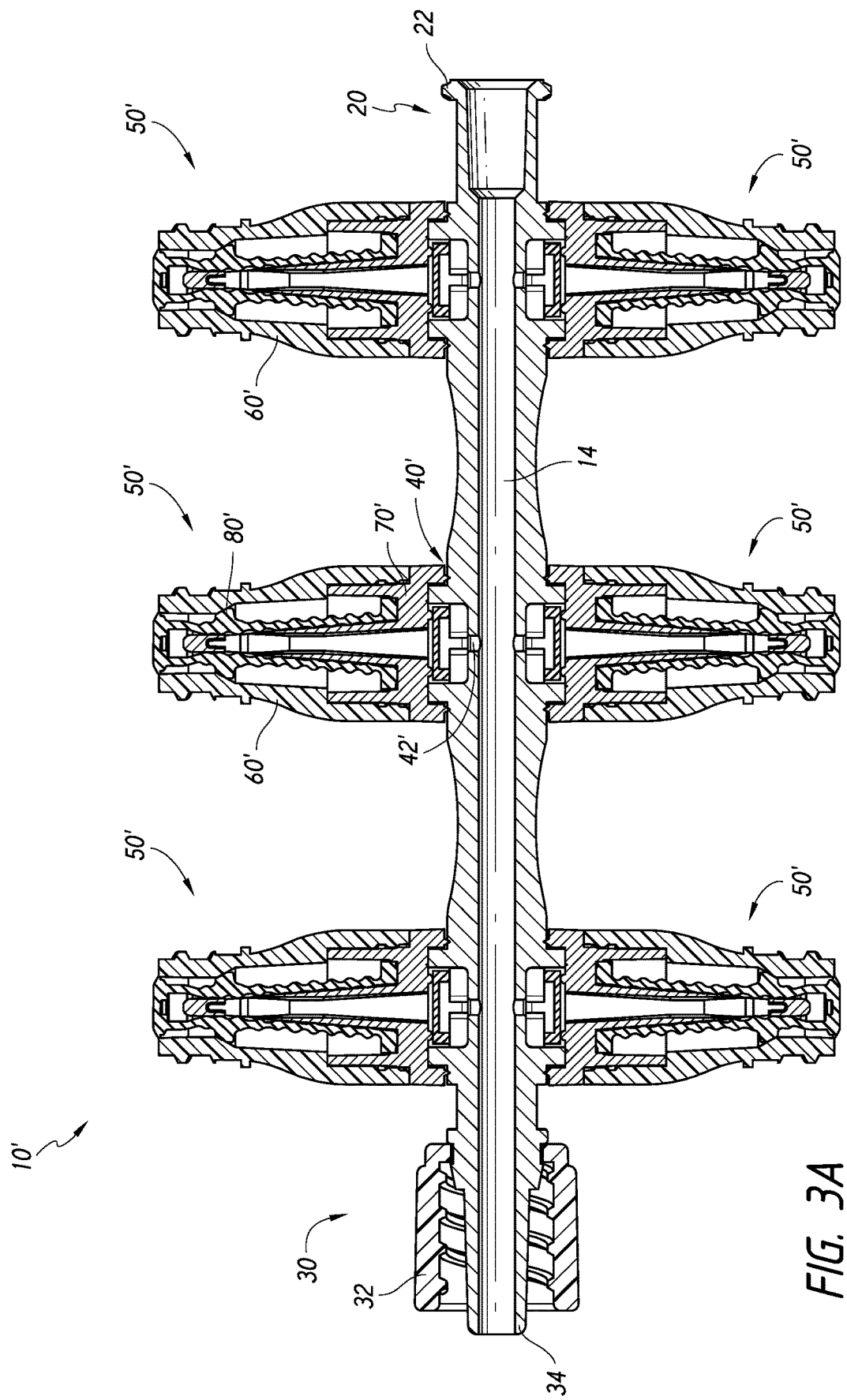
FIG. 3A is a cross-sectional view of the manifold of FIG. 1A.
Figure 4A:
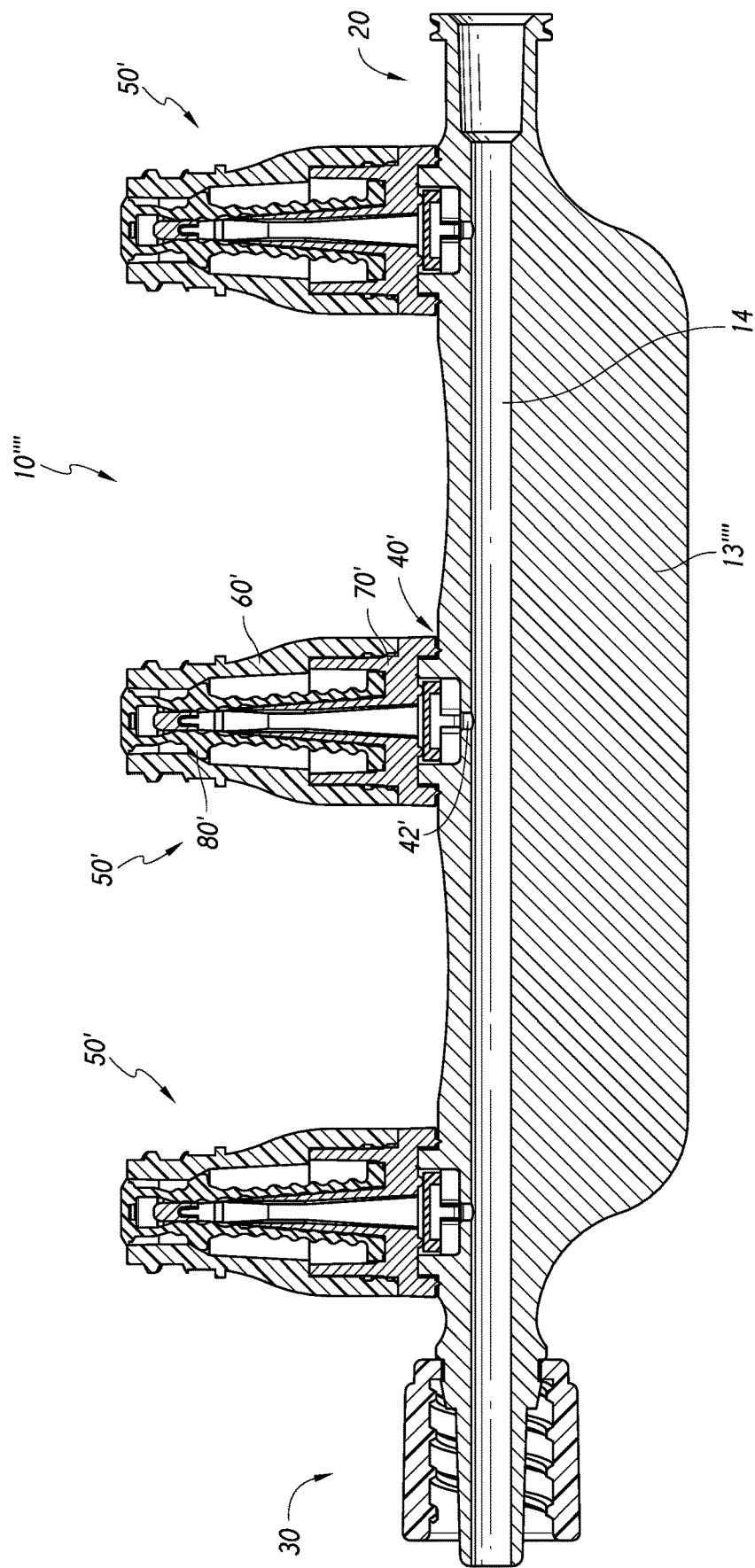
FIG. 4A is a cross-sectional view of the manifold of FIG. 2A.

FIGS. 3A and 4A illustrate cross-sectional views of the manifolds of FIGS. 1A and 2A, respectively. As illustrated, medical connectors 50' can attach to the manifold at access ports 40'. Similar to medical connector 50 discussed above, medical connector 50' can be a needleless medical connector that includes a connector body 60', a connector base 70', and a connector valve member 80' positioned at least partially within the connector body 60'. In some embodiments, the manifolds 10' and 10'''' shown in FIGS. 1A, 3A and 2A, 4A, respectively, can be modified to incorporate medical connectors 50.

Figure 3B:
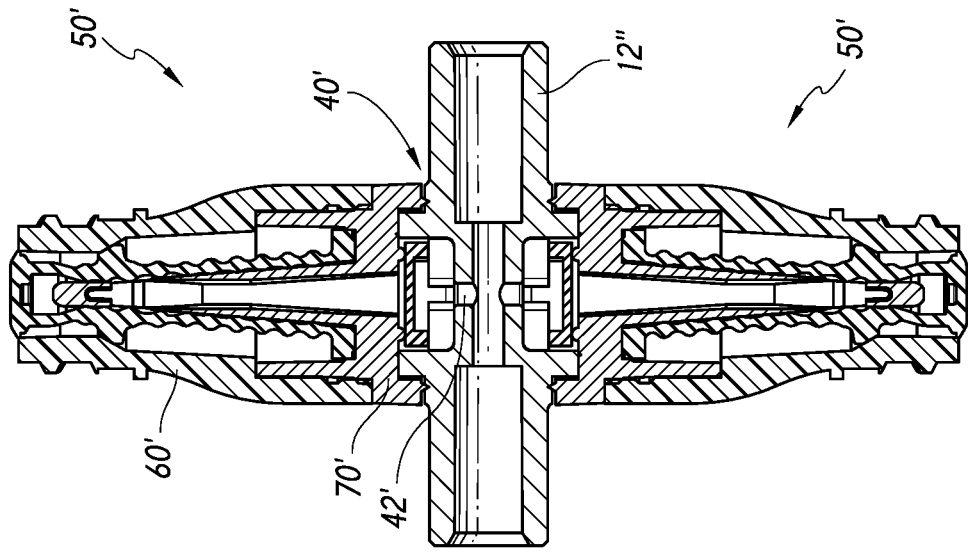
FIG. 3B is a cross-sectional view of the manifold of FIG. 1B.
Figure 4B:
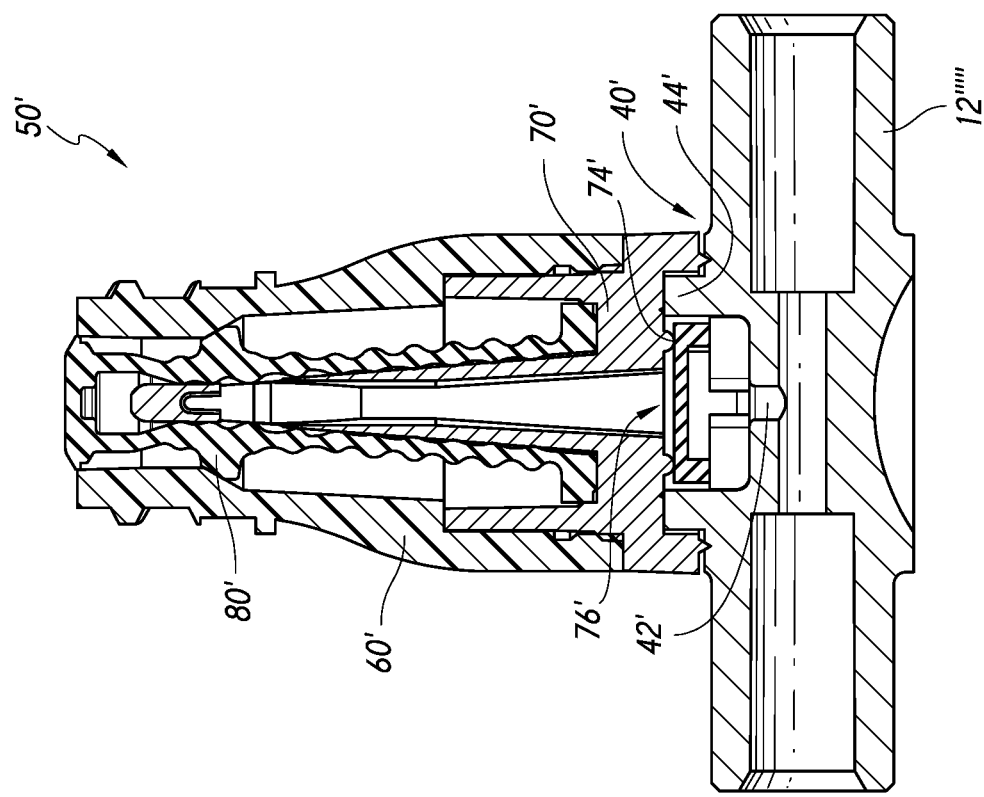
FIG. 4B is a cross-sectional view of the manifold of FIG. 2B.

FIGS. 3B and 4B illustrate cross-sectional views components of the manifolds shown FIGS. 1B and 2B, respectively. As illustrated, medical connectors 50' can attach to the manifold at access ports 40'. In some embodiments, the manifolds 10'' and 10''''' shown in FIGS. 1B, 3B and 2B, 4B, respectively, can be modified to incorporate medical connectors 50.

Medical connectors can be attached to the housings in a variety of ways. As shown in FIG. 4B for example, medical connector 50' can incorporate features to facilitate sonic welding of the connector to the housing. In the illustrated embodiment, medical connector 50' is attached to housing 12'''' by way of connector base 70'. An inner recess in connector base 70' is sized to receive projecting ring 44' of access port 40'. Projecting ring can help stabilize medical connector 50' on housing 12'''''.

Preferably, the medical connectors 50 can each provide a fluid flow path from a medical implement attached to the medical connector, through the medical connector, into the access port 40 and through an access channel 42 into a main channel 14 of the manifold. In a similar fashion, medical connectors 50' can each provide a fluid flow path from a medical implement attached to the medical connector, through the medical connector, and into the access port 40' and through an access channel 42' into a main channel 14 of the manifold. Preferably, the access port 40 or 40' can include a one-way valve or check valve 100, which can allow fluid to flow through the medical connector into the main channel 14, but prevent fluid from flowing from the main channel 14 back into the medical connector. Various embodiments of a check valve 100 are described in more detail below.

Figure 5:
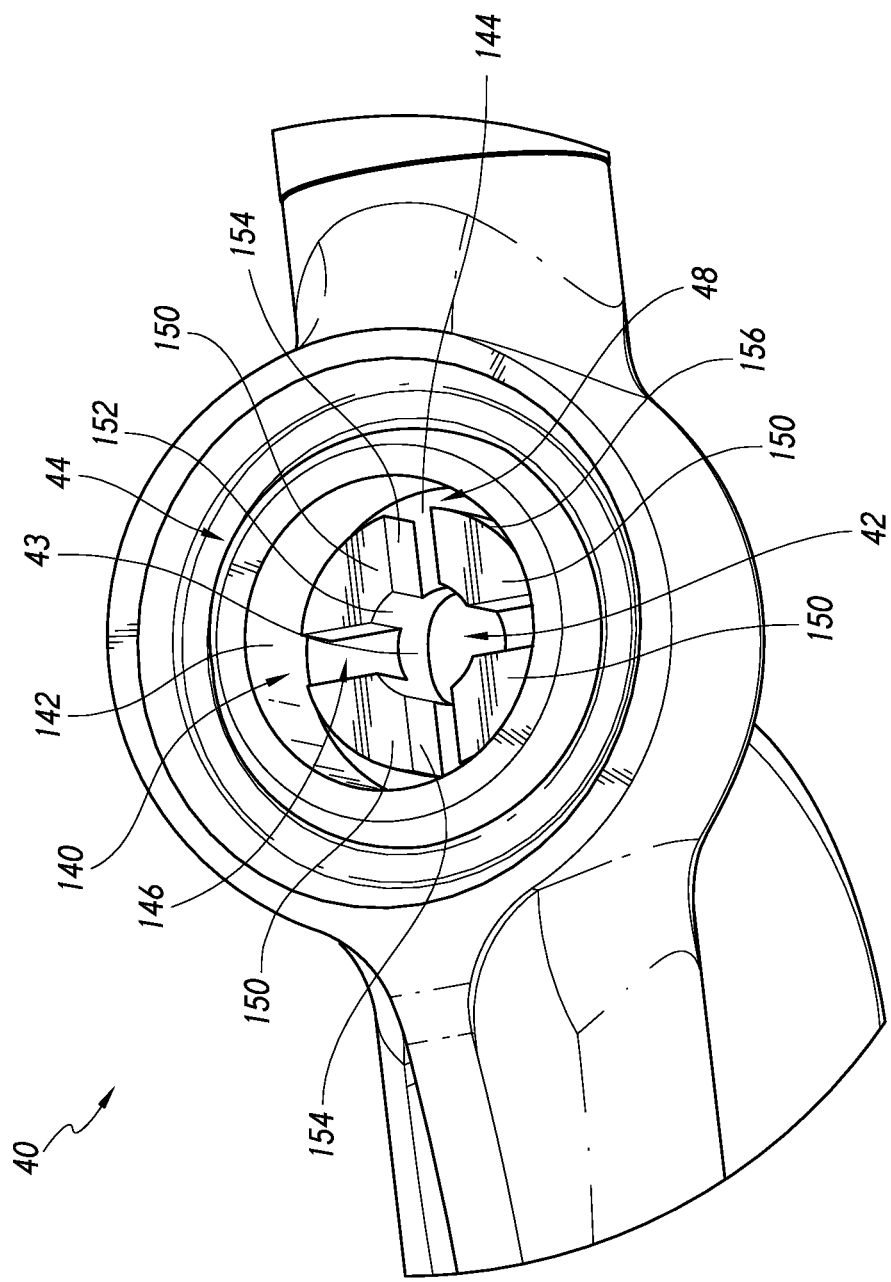
FIG. 5 is a perspective view of one embodiment of a port of a manifold.

FIG. 5 illustrates a perspective view of an access port 40 of a manifold. The access port can include a recess 140 with an outer wall 142 and a base 144. The recess is preferably cylindrical such that the outer wall is cylindrical, although in some embodiments it can have other shapes. An access channel 42 can connect the base 144 to a main channel of a manifold or other device. A plurality of protrusions 150 can extend upward from the base of the recess 140. The protrusions can each include a central wall 152 that faces the access channel 42, side walls 154, and an outer wall 156. In some embodiments, the central walls 152 of the protrusions can be flush with a side wall 43 of the access channel 42. In some embodiments, the central walls 152 can define a continuous surface with a side wall 43 of the access channel.

Preferably, the outer walls 156 of the protrusion do not extend all the way to the outer wall 142 of the access port recess 140, thereby defining an outer channel 48 between the protrusions and the outer wall 142. The protrusions can be spaced from each other to define transverse channels 46 between them that can connect the outer channel 48 to the access channel 42. In some embodiments, the access port 40 can also include an outer recess 44 that can be used to help seat a medical connector attached to the access port.

Figure 5A:
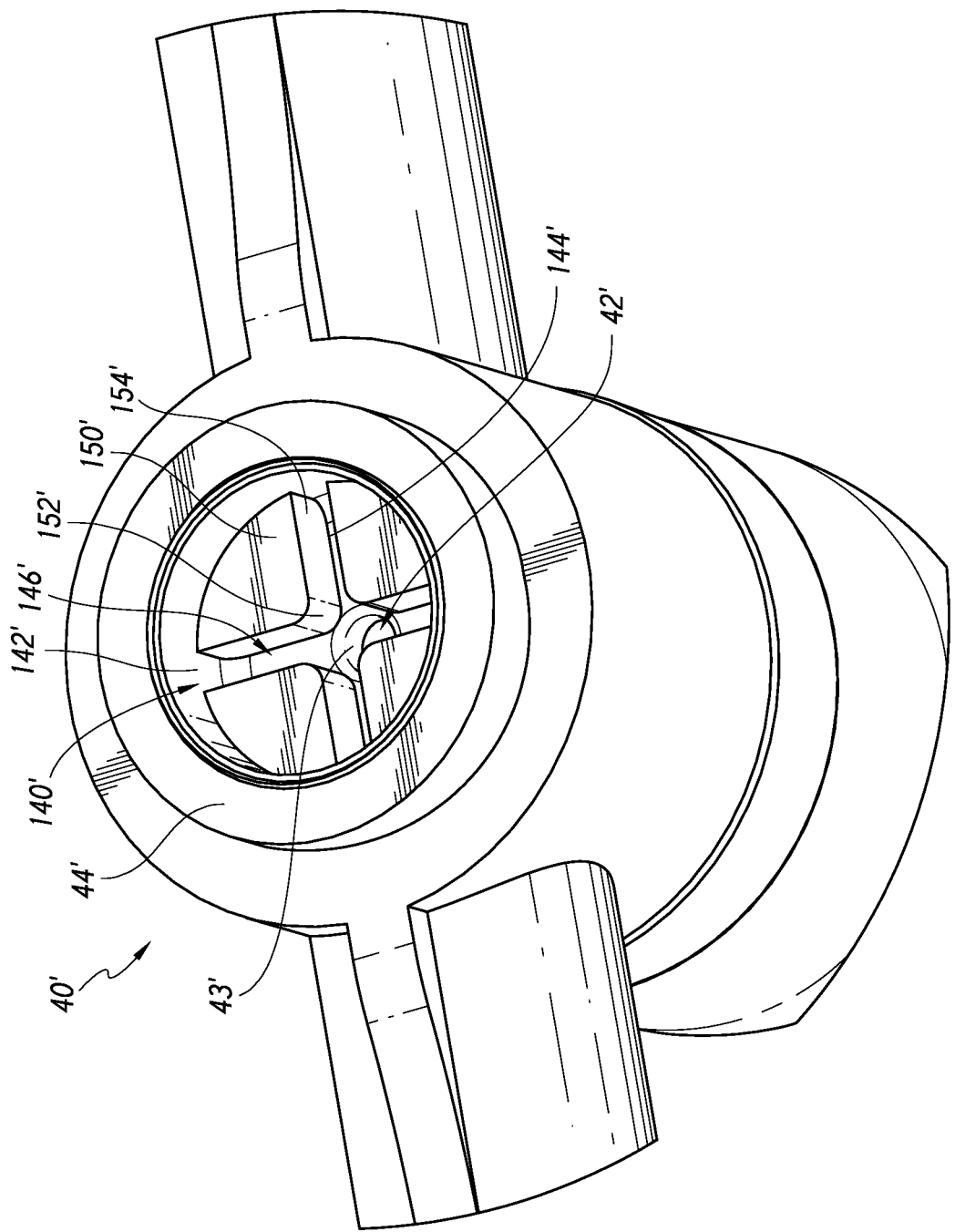
FIG. 5A is a perspective view of an embodiment of a port of a manifold.

FIG. 5A illustrates a perspective view of an access port 40' of a manifold which is similar in many respects to access port 40. The access port can include a recess 140' with an outer wall 142' and a base 144'. The recess is preferably cylindrical such that the outer wall is cylindrical, although in some embodiments it can have other shapes. An access channel 42' can connect the base 144' to a main channel of a manifold or other device. A plurality of protrusions 150' can extend upward from the base of the recess 140'. The protrusions can each include a central wall 152' that faces the access channel 42' and side walls 154'. In some embodiments, the central walls 152' of the protrusions can be recessed back from a side wall 43' of the access channel 42' as shown. The transition from the central walls 152' to the side wall 43' may be curved to facilitate fluid flow there through. In some embodiments, the central walls 152' can define a continuous surface with a side wall 43' of the access channel. As shown, the protrusions 150' may be formed flush with the outer wall 142' though in some embodiments, they may be off set from the wall and provide an outer fluid channel like channel 48 shown in FIG. 5. Access port 40' may also include projecting ring 44' that may be used to stabilize connector 50' as shown.

Figure 6:
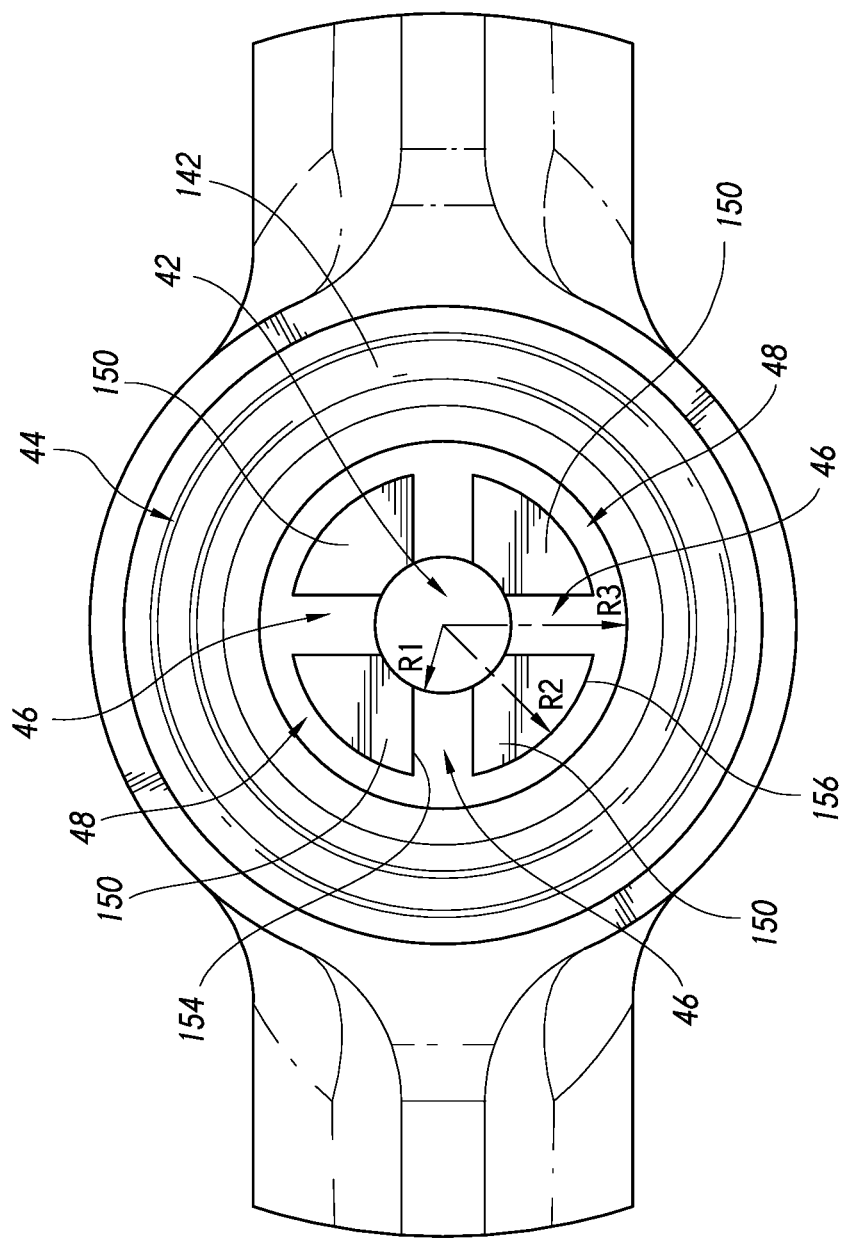
FIG. 6 is a top view of the port of FIG. 5.

FIG. 6 illustrates a top view of an access port 40. In the embodiment of FIG. 6, the access port includes four protrusions 150 that are spaced symmetrically about a center of the access channel 42. Preferably, side walls 154 of the protrusions are generally parallel to each other. In some embodiments, however, the side walls can angle toward each other as they get closer to the center of the access channel 42, and in some embodiments the side walls can diverge as they get closer toward the center of the access channel. In some embodiments, the access port 40 can include varying numbers of protrusions 50, such as 2, 3, 5, 6, or more protrusions. The protrusions can be symmetrically spaced about the access channel 42 or spaced about the access channel in other arrangements.

In some embodiments, various components of the access port 40 can be centered around the access channel 42. In some embodiments, the access channel itself can be generally cylindrical and have a radius $R_1$, as illustrated. In some embodiments the outer wall 142 of the access port recess 140 can have a radius $R_3$ centered on the center of the access channel 42. Similarly, the outer walls 156 of the protrusions 150 can be curved and have a radius of curvature R2 centered on the center of the access channel 42. Similar radius of curvatures may be defined by access port 40'. In the illustrated embodiment, R2' and R3' of access port 40' would be equal.

When fluid flows through a medical connector attached to an access port 40, it will flow through the channels of the access port in order to reach a main channel of a fluid flow line. In various embodiments, the sizing of certain components of the access port can affect the size of the outer channel 48, transverse channels 46, and/or access channel 42, and therefore can affect the fluid flow characteristics of the access port 40.

Thus, for example, in some embodiments the ratio of the radius $R_3$ of the access port recess 140 to the radius $R_2$ of the outer walls 156 of protrusions 150 may vary. In some embodiments, the ratio of $R_3$ to $R_2$ can be between approximately 0.5 and 2.0. In some embodiments, the ratio of $R_3$ to $R_2$ can be between approximately 0.8 and 1.7. In some embodiments, the ratio of $R_3$ to $R_2$ can be between approximately 1.0 and 1.5. In some embodiments, the ratio of $R_3$ to $R_2$ can be between approximately 1.1 and 1.3. These ratios are also applicable to access port 40'.

Similarly, in some embodiments the ratio of the radius $R_3$ of the access port recess 140 to the radius $R_1$ of the access channel 42 may vary. In some embodiments, the ratio of $R_3$ to $R_1$ can be between approximately 2.0 and 3.3. In some embodiments, the ratio of $R_3$ to $R_1$ can be between approximately 2.3 and 3.0. In some embodiments, the ratio of $R_3$ to $R_1$ can be between approximately 2.5 and 2.8. In some embodiments, the ratio of $R_3$ to $R_1$ can be between approximately 2.6 and 2.7. These ratios are also applicable to access port 40'.

Further, in some embodiments the ratio of the radius $R_2$ of the outer walls 156 of protrusions 150 to the radius $R_1$ of the access channel 42 may vary. In some embodiments, the ratio of $R_2$ to $R_1$ can be between approximately 1.5 and 2.9. In some embodiments, the ratio of $R_2$ to $R_1$ can be between approximately 1.8 and 2.6. In some embodiments, the ratio of $R_2$ to $R_1$ can be between approximately 2.1 and 2.3. These ratios are also applicable to access port 40'.

Figure 7:
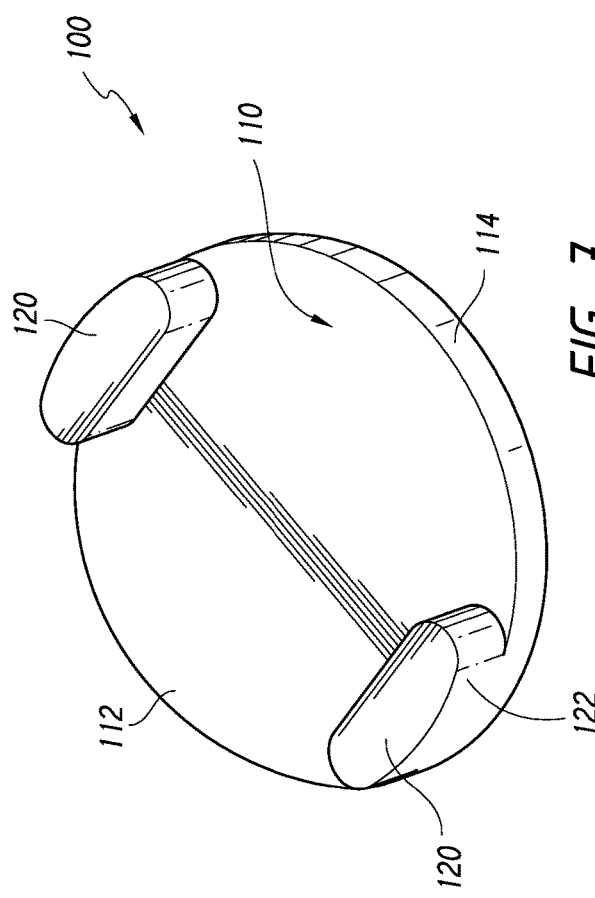
FIG. 7 is a bottom perspective view of one embodiment of a check valve.
Figure 8:
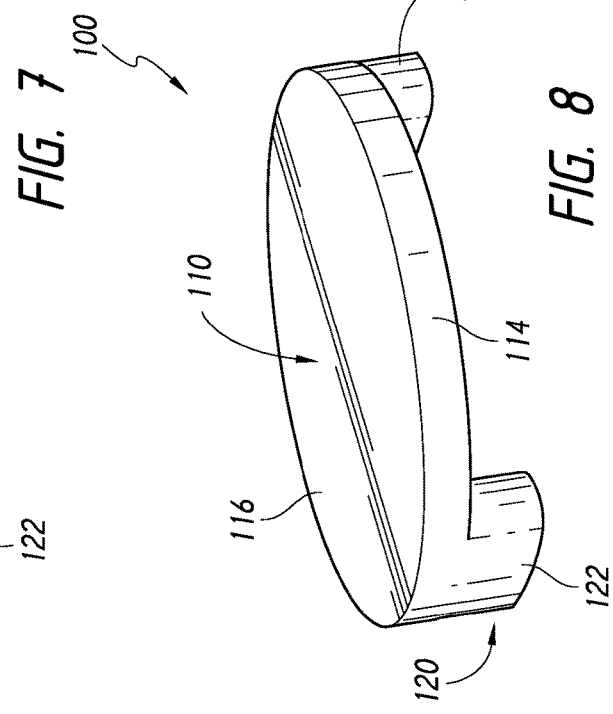
FIG. 8 is a top perspective view of the check valve of FIG. 7.

FIGS. 7 and 8 illustrate perspective views of a check valve 100 that can be positioned within an access port 40 or 40'. FIG. 7 illustrates a bottom perspective view and FIG. 8 illustrates a top perspective view. The check valve preferably includes a diaphragm 110 having a bottom or lower surface 112, a side wall 114, and a top or upper surface 116. The diaphragm is preferably solid, although in some embodiments it can have perforations. A plurality of supports 120 can extend from the bottom or lower surface 112 of the diaphragm. The supports can be used to provide space for the diaphragm to flex from a closed to an open position, discussed in more detail below. Preferably, the diaphragm and supports are integrally formed (e.g., they may be molded as a single piece), although in some embodiments they may be formed of separate components.

The supports can have an outer wall 122 that is preferably flush with and forms a continuous surface with the side wall 114 of the diaphragm. In some embodiments, however, the supports 120 can be inset from the side wall 114 such that there is a portion of the bottom surface 112 between the supports 120 and the side wall 114.

Figure 9:
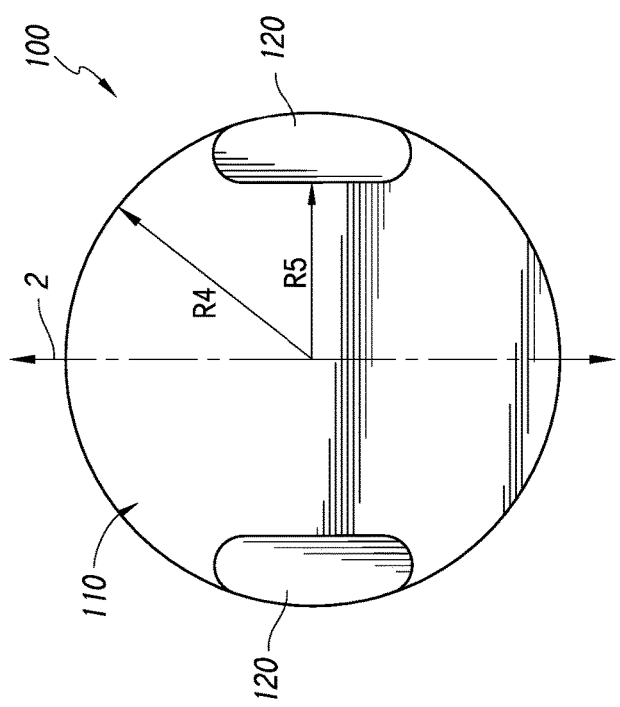
FIG. 9 is a bottom view of the check valve of FIG. 8.

FIG. 9 illustrates a bottom view of the valve 100. The valve is preferably circular with a radius $R_4$, although in some embodiments the valve can have other shapes, such as a square, oval, rectangle, etc. In some embodiments, the radius $R_4$ can be approximately equal to the radius $R_3$ of the access port recess 140, such that the valve 100 can fit flush within the recess. In some embodiments, the radius $R_4$ can be slightly or substantially smaller than the radius $R_3$ such that a gap exists between the side walls 114 of the valve 100 and the side walls 142 of the access port recess when the valve is centered in the access port recess. The existence of a gap can make manufacturing of the valve easier. Varying the size of the gap can also affect flow rates through the valve. In some embodiments, the radius $R_4$ can be between approximately 0.02 inches and approximately 0.09 inches smaller than the radius $R_3$. In some embodiments, the radius $R_4$ can be between approximately 0.03 inches and approximately 0.08 inches smaller than the radius $R_3$. In some embodiments, the radius $R_4$ can be between approximately 0.05 inches and approximately 0.06 inches smaller than the radius $R_3$.

In some embodiments, as illustrated, the supports 120 can be positioned approximately 180 degrees apart about the center of the valve. The valve can have an axis of symmetry 2 that bisects the valve and does not pass through either support, as illustrated. In some embodiments, the valve can have more than two supports 120, with pairs positioned approximately 180 degrees apart from each other. For example, a valve could have four supports, each 90 degrees apart, and multiple axes of symmetry that bisect the valve and do not pass through any of the supports. In some embodiments, the axis of symmetry can define how the valve deforms if it experiences a pressure differential between its bottom surface 112 and its top surface 116. For example, in the illustrated embodiment, a positive net pressure on the top surface of the valve member would cause the valve member to bend, buckle, or curve generally about the axis of symmetry or an axis that is parallel to the axis of symmetry.

In some embodiments, the supports 120 can all be positioned the same minimum distance $R_5$ from the center of the valve. In some embodiments, one or more of the supports can have a different minimum distance from the center of the valve than one or more of the other supports, in which case $R_5$ can refer to the minimum distance from the center of the valve to the closest support 120. In some embodiments, the relationship between the distance $R_5$ and $R_4$ can affect how easily the valve member deforms as a result of differential pressures on the top surface 116 and bottom surface 112 of the diaphragm 110. In some embodiments, for example, the ratio of $R_4$ to $R_5$ can be between approximately 1.2 and approximately 1.8. In some embodiments, the ratio of $R_4$ to $R_5$ can be between approximately 1.3 and approximately 1.6. In some embodiments, the ratio of $R_4$ to $R_5$ can be between approximately 1.3 and approximately 1.5. In some embodiments, the ratio of $R_4$ to $R_5$ can be between approximately 1.35 and approximately 1.45. In some embodiments, the ratio of $R_4$ to $R_5$ can be greater than 1.8 or less than 1.2.

Figure 10:
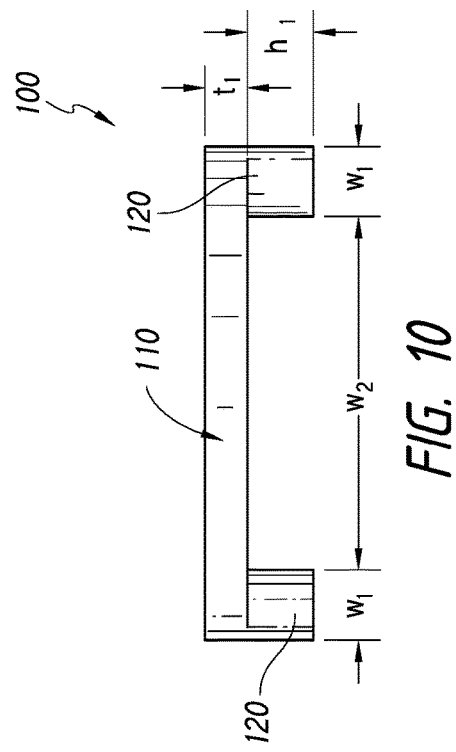
FIG. 10 is a side view of the check valve of FIG. 9.

FIG. 10 illustrates a side view of the valve 100, oriented such that the axis of symmetry 2 is perpendicular to the illustrated plane. In various embodiments, the sizing of the diaphragm 110 and supports 120 can be modified to adjust the pressure differential required for the valve member to bend or buckle. For example, the supports can have a width $w_1$ and the distance between the supports can have a width $w_2$. Similarly, the diaphragm can have a thickness $t_1$ and the supports can have a height $h_1$. In some embodiments, the ratio of the width $w_2$ to the thickness $t_1$ can affect the ability of the valve to resist pressure differentials. In some embodiments, the ratio of the width $w_2$ to the thickness $t_1$ can be between approximately 7 and approximately 10. In some embodiments, the ratio of the width $w_2$ to the thickness $t_1$ can be between approximately 7.5 and approximately 9.5. In some embodiments, the ratio of the width $w_2$ to the thickness $t_1$ can be between approximately 8 and approximately 9. In some embodiments, the ratio of the width $w_2$ to the thickness $t_1$ can be between approximately 8.2 and approximately 8.5.

In some embodiments, the ratio of the width $w_2$ to the height $h_1$ of the supports can affect how easily and how much the diaphragm 110 can bend when the valve is in an open position, discussed below. This can also affect the ability of the valve to handle high flow rates and/or how quickly the valve opens to allow fluid flow. In some embodiments, the ratio of the width $w_2$ to the height $h_1$ can be between approximately 3 and approximately 8. In some embodiments, the ratio of the width $w_2$ to the height $h_1$ can be between approximately 4 and approximately 7. In some embodiments, the ratio of the width $w_2$ to the height $h_1$ can be between approximately 4.5 and approximately 6.5. In some embodiments, the ratio of the width $w_2$ to the height $h_1$ can be between approximately 5 and approximately 6.

Figure 11B:
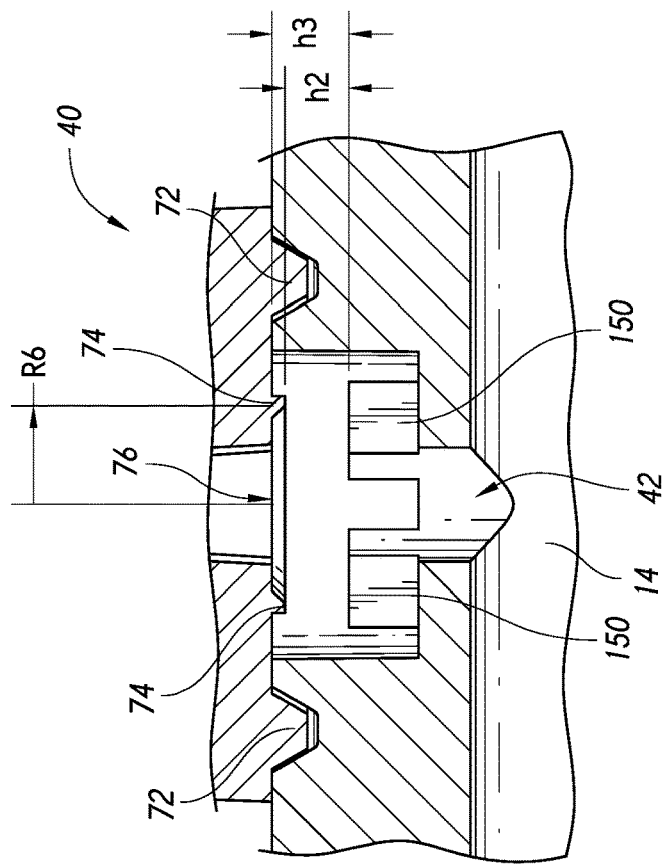
FIG. 11B is a cross-sectional view of one embodiment of a port of a manifold with an attached medical connector, with a check valve not shown.
Figure 11A:
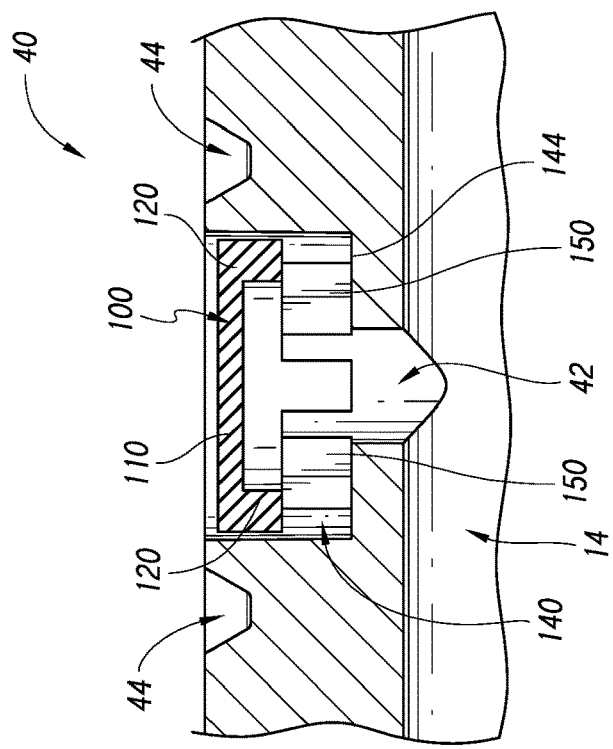
FIG. 11A is a cross-sectional view of one embodiment of a port of a manifold with a check valve.

FIG. 11A illustrates a valve 100 positioned within an access port 40, as described above. The supports 120 can be positioned on the protrusions 150 to lift the diaphragm above the protrusions. In some embodiments, the access port recess 140 can have no protrusions and the supports of the valve can be positioned directly on the base 144 of the recess or on the base of any recessed portion of a flow channel. Thus, for example, in some embodiments the valve can be positioned within an inlet and/or an outlet port of a manifold, extension set, or other connection systems. In some embodiments, the valve can be positioned within a medical connector that has only a single inlet and outlet port.

FIG. 11B illustrates a cross-sectional view of an access port 40 that has a medical connector attached to the access port. The access port can have a valve 100, which is not shown for illustrative purposes. As shown in FIG. 11B, when a medical connector is attached to an access port there can be a height $h_2$ between a ring 74 of the medical connector and a top surface of the protrusions 150 extending from the base of the recess 140. There can also be a height $h_3$ between a bottom surface of the base 70 of the medical connector (excluding any ring 74) and the top surface of the protrusions 150. Also visible in FIG. 11B is an inner radius $R_6$ of the ring 74 of the medical connector (i.e., a radius from the center of the ring to an inner surface of a wall that forms the ring).

Figure 12B:
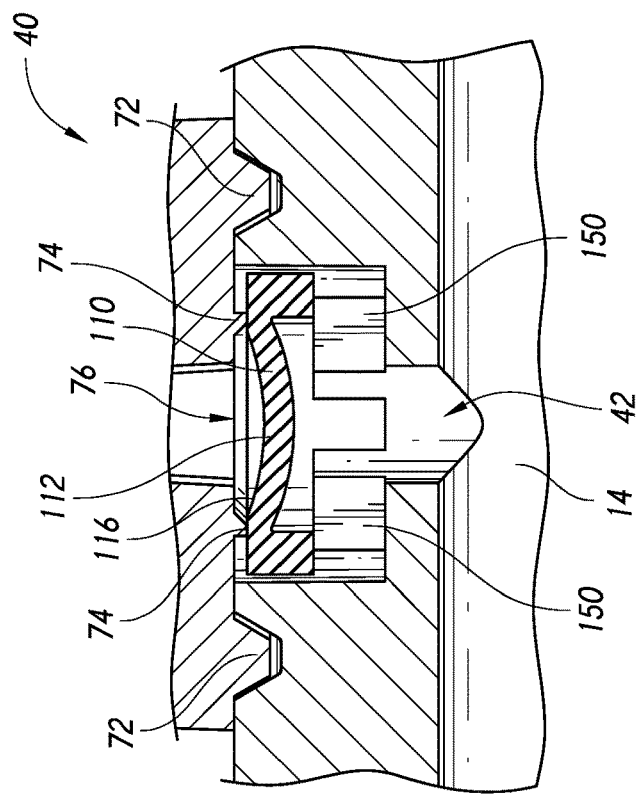
FIG. 12B is a cross-sectional view of the embodiment of FIG. 12A with the check valve in an open position.
Figure 12A:
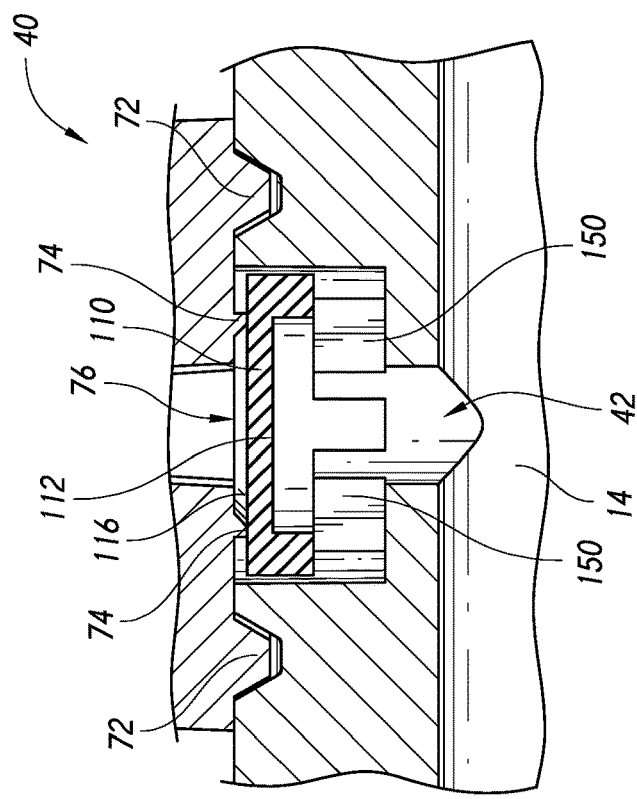
FIG. 12A is a cross-sectional view of one embodiment of a port of a manifold with an attached medical connector and a check valve in a closed position.

FIGS. 12A and 12B illustrate a cross-sectional view of an access port 40 that includes a valve member 100 and that has a medical connector 50 attached to the access port. In some embodiments, a base 70 of the medical connector can have an annular projection 72 that can be used to help attach the medical connector to the access port such as by sonic welding or gluing. Other forms of attachment are also possible, including snap fit constructions. In the illustrated embodiment, projection 72 is preferably glued into outer recess 44.

FIG. 12A illustrates the valve member 100 in a closed position and FIG. 12B illustrates the valve member in an open position. The valve is oriented the same as in FIG. 10, such that the axis of symmetry of the valve is perpendicular to the plane of the figure. In the closed position, the diaphragm 112 of the valve can be generally flat on both sides and can seal against the base 70 of the medical connector. In some embodiments, as illustrated, the medical connector can have a ring 74 or other projection that can be sized and configured to contact and seal against the diaphragm 110 of the valve 100 when the valve is in a closed position. As shown in FIG. 4B, medical connector 50' may include a similar ring 74'.

In some embodiments, the medical connector 50 and/or the access port 40 can be sized and configured such that the base 70 of the medical connector or the ring 74 can compress at least a portion of the valve 100. This can help create the seal between the diaphragm 110 and the medical connector. Thus, in embodiments where the diaphragm seals against a ring 74 or other projection of the medical connector, the height $h_2$ (shown in FIG. 11B) can be less than the total height of the valve member 100 (i.e., the sum of $h_1$ and $t_1$, illustrated in FIG. 10). Similarly, in embodiments where the connector does not have a ring or other projection, the height $h_3$ (shown in FIG. 11B) can be less than the total height of the valve member. In various embodiments, the relative differences between the heights can affect the amount of sealing. For example, in some embodiments the ratio of the total height of the valve member to the height $h_2$ can be between approximately 1.0 and approximately 1.5. In some embodiments, the ratio of the total height of the valve member to the height $h_2$ can be between approximately 1.0 and approximately 1.3. In some embodiments, the ratio of the total height of the valve member to the height $h_2$ can be between approximately 1.0 and approximately 1.2. In some embodiments, the ratio of the total height of the valve member to the height $h_2$ can be between approximately 1.1 and approximately 1.2. In embodiments without a sealing ring 74 or other projection, various ratios of the total height of the valve member to the height $h_3$ can be as described with respect to the height $h_2$. In some embodiments, the total height of the valve member can be less than the height $h_2$ such that the valve member functions as a floating check valve. In some such instances, the supports 120 on the bottom surface of the diaphragm 110 may provide stability and prevent inversion of the diaphragm. Similar ratios are applicable to medical connector 50'.

In various embodiments, the relationship between the radius $R_6$ of a ring 74 (shown in FIG. 11B) and the distance $R_5$ between supports 120 and the center of the valve (shown in FIG. 10) can affect how the valve deforms in response to a compressive force from the ring and any resulting change in a seal between the ring and the valve and/or in a cracking pressure of the valve (described further below). Preferably, $R_5$ can be approximately equal to $R_6$. In some embodiments, $R_5$ can be smaller than $R_6$. In some embodiments, $R_5$ can be greater than $R_6$. In some embodiments, the relationship between $R_5$ and $R_6$ can be varied according to the durometer of the check valve 100 in order to ensure that the valve seals as desired. Similar adjustments can be made to medical connector 50'.

If a negative pressure differential exists on the diaphragm between the bottom surface 112 and the upper or top surface 116—i.e., a net negative pressure on the top surface—the pressure will tend to push the diaphragm against the base 70 or inner annular projection 74, which can create or enhance a seal and prevent fluid from flowing into the medical connector. In contrast, if there is a positive pressure differential—i.e., a positive net pressure on the top surface 116—the diaphragm 110 will tend to deform as described above and move the valve from a closed to an open position, as illustrated in FIG. 12B. In the open position, the valve can flex downward (creating a concavity on its top surface), allowing fluid to flow through an opening 76 in the base of the medical connector, into the access port recess 140, and through the access channel 42 to reach the main channel 14.

In some embodiments, at least a portion of the valve member 100 remains stationary as the valve transitions between an open and closed position. This can help the valve move more easily from an open to a closed position to help prevent undesired retrograde flows. It can also allow for designs that transition from a closed to an open position at lower pressures, as described further below. In some embodiments, at least a portion of the diaphragm can remain in generally the same location when the valve is in an open position as when the valve is in a closed position. In some embodiments, at least a portion of the diaphragm 110 can remain in contact with the base 70 of a medical connector when the valve is in the open position.

In some embodiments, the valve 100 can be formed of a resilient material such that, absent a pressure differential, the valve tends to move toward the closed position (i.e., is biased toward the closed position).

As described above, the valve can be designed differently to affect how easily it moves from a closed to an open position. The pressure differential required to move the valve 100 from a closed to an open position can be referred to as the cracking pressure. In some embodiments, the valve can have a minimal cracking pressure, such that the valve very easily transitions from a closed to an open position. This can make it easier to pass fluids through the valve and into a main fluid flow line. It also allows the valves to work effectively with high flow rate connectors (such as, for example, connectors that allow flow rates of 450 mL/min or even greater). In some embodiments, the valve can have a cracking pressure that is at or below approximately 5 psi. In some embodiments, the valve can have a cracking pressure that is at or below approximately 4 psi. In some embodiments, the valve can have a cracking pressure that is at or below approximately 3 psi. In some embodiments, the valve can have a cracking pressure that is at or below approximately 2 psi. In some embodiments, the valve can have a cracking pressure that is at or below approximately 1 psi. In some embodiments, the valve can have a cracking pressure that is less than the pressure exerted on the valve from fluid in a reservoir hanging on a standard IV pole. In some embodiments, this can be approximately equal to the pressure of 36 inches of water. In some embodiments, this can be approximately equal to 1.3 psi.

In some embodiments, the cracking pressure can be zero, such that even with zero pressure differential between the lower 112 and upper 116 surfaces of the diaphragm 110 the valve will be in an open position. In other words, in some embodiments the closed position of the valve is not an equilibrium position of the valve. In such embodiments, the valve may not be in a closed position until a retrograde fluid flow creates a negative pressure differential on the diaphragm 110. In some embodiments with a zero cracking pressure, the valve can function as a floating check valve, as described, for example, above.

Figure 13A:
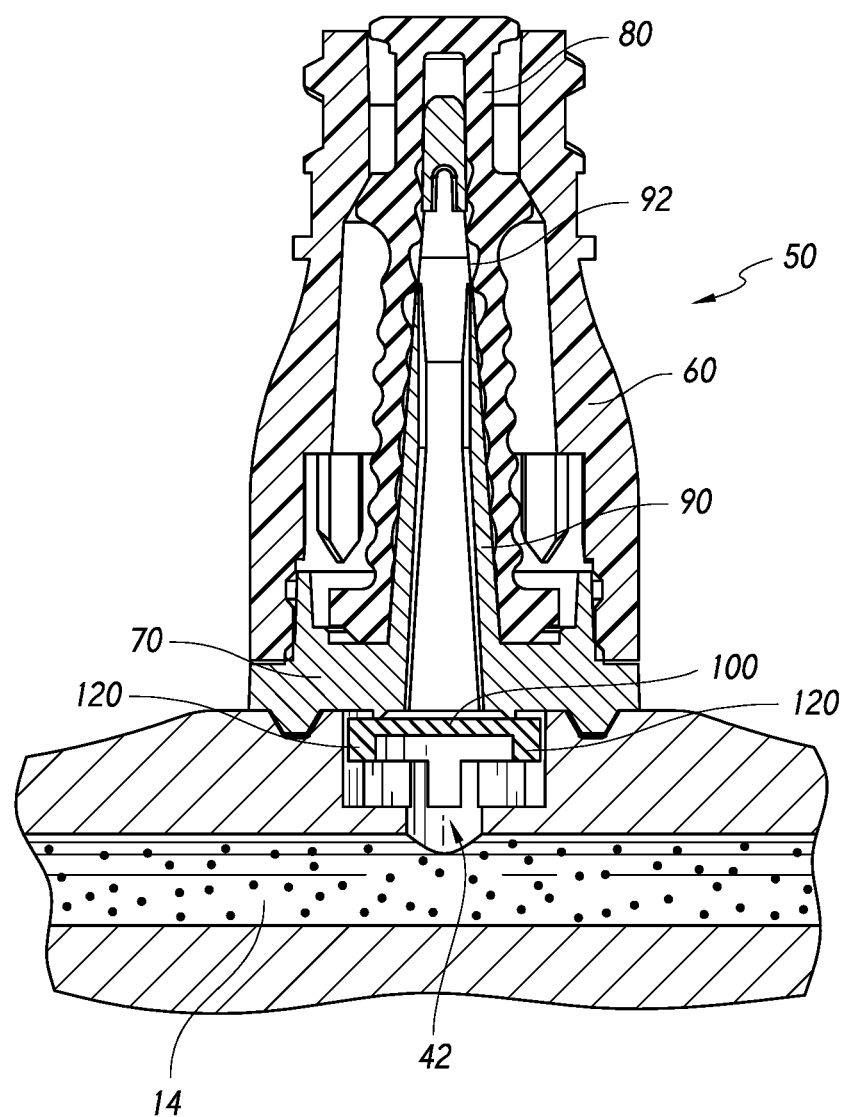
FIG. 13A is a cross-sectional view of one embodiment of a port of a manifold with an attached medical connector and a check valve in a closed position.
Figure 13B:
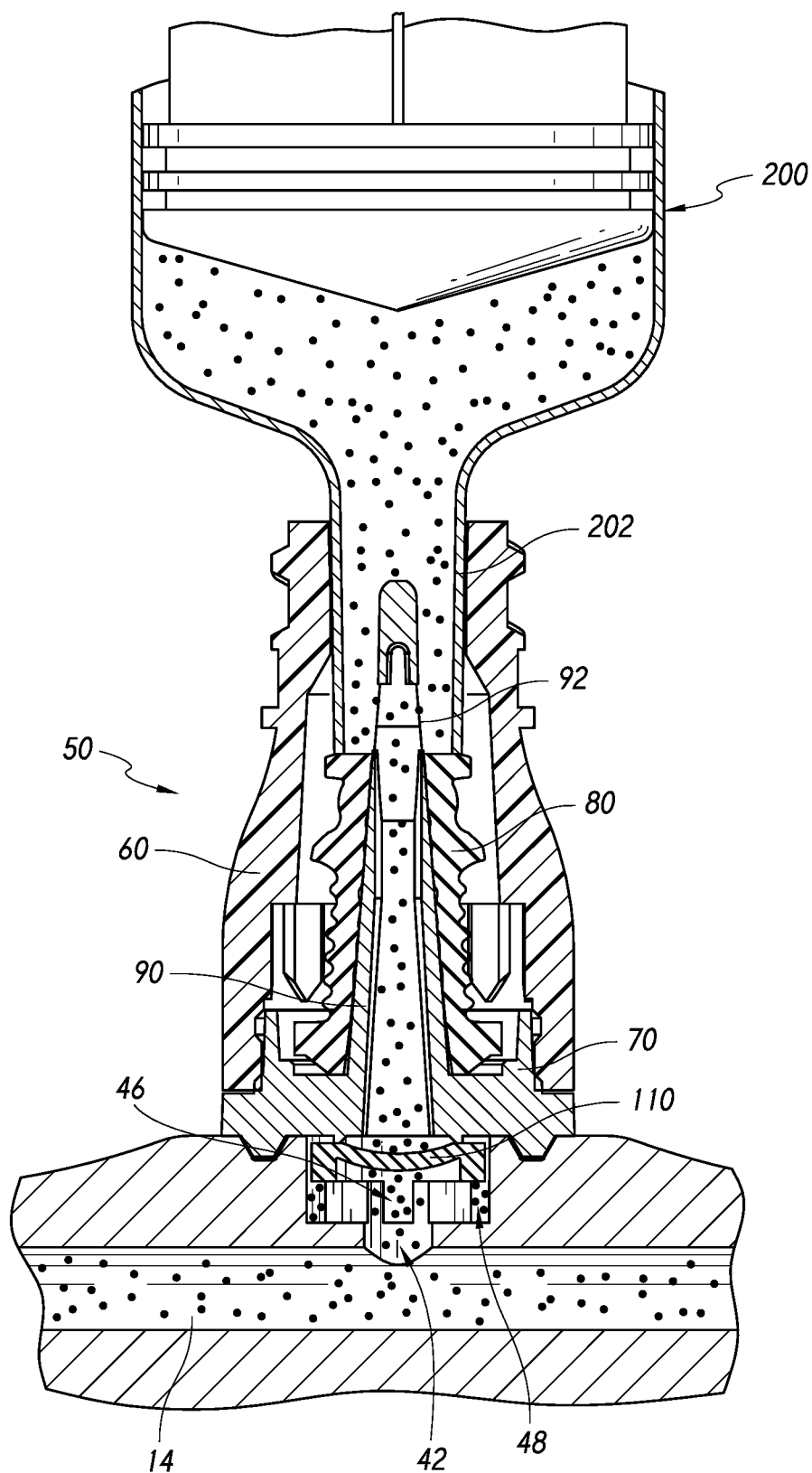
FIG. 13B is a cross-sectional view of the embodiment of FIG. 13A with the check valve in an open position.

FIGS. 13A and 13B illustrate a cross-sectional view of an access port 40 that includes a valve 100 and that has a medical connector attached to the access port. FIGS. 13A and 13B are similar to FIGS. 12A and 12B, but include an illustration of the entirety of a medical connector 50 that can be attached to the access port. Additionally, FIG. 13A illustrates the valve 100 in a closed position and FIG. 13B illustrates a medical implement 200 connected to the medical connector.

As described above, in some embodiments the medical connector 50 can be a needleless connector that has a base 70, a body 60, and a connector valve member 80. The base can also include an internal projection 90 that is within the body 60. A cannula 202 of the medical implement can compress the connector valve member 80 into an open position, exposing an opening 92 in the internal projection through which fluid in the cannula can pass. Once within the internal projection, the fluid can flow into the access port recess 140, through the access channel 42, and into the main flow channel 14. Similar activation can occur with medical connector 50'.

In some embodiments, one or more components of the devices and elements described herein can be translucent, transparent, and/or clear such that the fluid flow path through the components is visible. These components can include, for example, the housing 12 of a manifold, the medical connector 50 (including the body 60, base 70, and/or valve member 80), the medical connector 50' (including the body 60', base 70', and/or valve member 80'), and/or the check valve 100. Additionally, in some embodiments one or more components can include elements configured or adapted to kill pathogens. For example, in some embodiments one or more of the valves 80, 80', or 100 can include antimicrobial agents. In some embodiments, the antimicrobial agents can be a coating or can be incorporated into the structure of the components, from where they can leach out, such as from a silicone matrix of a valve.

The terms "approximately", "about", and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

Similarly, this method of disclosure is not to be interpreted as reflecting an intention that any claim require more features than are expressly recited in that claim. Rather, inventive aspects may lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A medical check valve for use in a medical device to provide one-way fluid flow between a first fluid location and a second fluid location, said check valve comprising:
   a flexible diaphragm comprising a top surface, a bottom surface, and a side wall between the top surface and the bottom surface;
   a first support member extending from the bottom surface of the flexible diaphragm and a second support member extending from the bottom surface of the flexible diaphragm, the first support member and second support member positioned to define a line of symmetry that bisects the bottom surface without passing through the first support member or the second support member;
   wherein the flexible diaphragm has a first position in which the top surface is generally planar and is configured to seal against a fluid opening and a second position in which a portion of the diaphragm is curved between the first and second support members to form a concavity in the top surface about the line of symmetry and is configured to be displaced from the fluid opening.

2. The medical check valve of claim 1, wherein the line of symmetry is the only line of symmetry that bisects the bottom surface without passing through the first support member or the second support member.

3. The medical check valve of claim 1, wherein the flexible diaphragm is a disc.

4. The medical check valve of claim 3, wherein the first and second support members are positioned 180 degrees apart about the disc.

5. The medical check valve of claim 1, wherein the flexible diaphragm is nonperforate.

6. The medical check valve of claim 1, wherein the flexible diaphragm, the first support member, and the second support member are integrally formed.

7. The medical check valve of claim 1, wherein a net pressure of less than 3 psi on the top surface of the flexible diaphragm is sufficient to move the diaphragm from the first position to the second position.

8. The medical check valve of claim 7, wherein a net pressure of less than 1 psi on the top surface of the flexible diaphragm is sufficient to move the diaphragm from the first position to the second position.

9. The medical check valve of claim 8, wherein a positive net pressure on the bottom surface of the flexible diaphragm is needed to maintain the flexible diaphragm in the first position.

10. The medical check valve of claim 1, wherein no support members other than the first and second support members extend from the bottom surface of the flexible diaphragm.

11. A medical manifold comprising:
    a fluid channel;
    a port in fluid communication with said fluid channel, wherein the port is configured to be connected to a medical connector; and
    a check valve positioned in said port and comprising:
       a flexible diaphragm comprising a top surface, a bottom surface, and a side wall between the top surface and the bottom surface; and
       a first support member extending from the bottom surface of the flexible diaphragm and a second support member extending from the bottom surface of the flexible diaphragm, the first support member and second support member positioned to define a line of symmetry that bisects the bottom surface without passing through the first support member or the second support member;
    wherein the flexible diaphragm has a first position in which the top surface is generally planar and is configured to seal against a fluid opening in fluid communication with the medical connector when the medical connector is connected to the port and a second position in which the top surface of the diaphragm is curved around the line of symmetry and is configured to be displaced from the fluid opening; and
    wherein the first and second support members remain in generally the same location in said port when the flexible diaphragm is in the first and second positions.

12. The medical manifold of claim 11, wherein the line of symmetry is the only line of symmetry that bisects the bottom surface without passing through the first support member or the second support member.

13. The medical manifold of claim 11, wherein the flexible diaphragm is a disc.

14. The medical manifold of claim 13, wherein the first and second support members are positioned 130 degrees apart about the disc.

15. The medical manifold of claim 11, wherein the flexible diaphragm is nonperforated.

16. The medical manifold of claim 11, wherein the flexible diaphragm, the first support member, and the second support member are integrally formed.

17. The medical manifold of claim 11, wherein a net pressure of less than 3 psi on the top surface of the flexible diaphragm is sufficient to move the diaphragm from the first position to the second position.

18. The medical manifold of claim 17, wherein a net pressure of less than 1 psi on the top surface of the flexible diaphragm is sufficient to move the diaphragm from the first position to the second position.

19. The medical manifold of claim 18, wherein a positive net pressure on the bottom surface of the flexible diaphragm is needed to maintain the flexible diaphragm in the first position.

20. The medical manifold of claim 11, wherein no support members other than the first and second support members extend from the bottom surface of the flexible diaphragm.

* * * * *

UNITED STATES PATENT AND TRADEMARK OFFICE
CERTIFICATE OF CORRECTION

| | |
|---|---|
| PATENT NO. | : 11,364,372 B2 |
| APPLICATION NO. | : 16/449124 |
| DATED | : June 21, 2022 |
| INVENTOR(S) | : David Nelson |

It is certified that error appears in the above-identified patent and that said Letters Patent is hereby corrected as shown below:

On the Title Page

Page 2, Column 1 (Item (56) U.S. Patent Documents), Line 18, delete "Brass" and insert -- Bross --.

Page 4, Column 1 (Item (56) U.S. Patent Documents), Line 37, delete "1/1997" and insert -- 10/1997 --.

Page 5, Column 2 (Item (56) U.S. Patent Documents), Line 30, delete "Mosier" and insert -- Mosler --.

Page 5, Column 2 (Item (56) U.S. Patent Documents), Line 72, delete "Fang," and insert -- Fangrow, --.

Page 6, Column 1 (Item (56) U.S. Patent Documents), Line 75, delete "Slopes" and insert -- Siopes --.

Page 7, Column 1 (Item (56) U.S. Patent Documents), Line 32, delete "Niedospial" and insert -- Niedospial, Jr. --.

Page 7, Column 2 (Item (56) U.S. Patent Documents), Line 17, delete "Fang," and insert -- Fangrow, --.

Page 7, Column 2 (Item (56) U.S. Patent Documents), Line 28, delete "Bernard" and insert -- Burnard --.

Page 8, Column 1 (Item (56) U.S. Patent Documents), Line 72, delete "Mosier" and insert -- Mosler --.

Page 8, Column 2 (Item (56) Other Publications), Line 9, delete "BackcheckValve," and insert -- Backcheck Valve, --.

Signed and Sealed this
Twenty-seventh Day of September, 2022

*Katherine Kelly Vidal*

Katherine Kelly Vidal
*Director of the United States Patent and Trademark Office*

CERTIFICATE OF CORRECTION (continued)
U.S. Pat. No. 11,364,372 B2

In the Specification

Column 6, Line 9, delete "16'''" and insert -- 16"" --.

In the Claims

Column 16, Line 34 (approx.), Claim 14, delete "130" and insert -- 180 --.